(12) United States Patent
Singh et al.

(10) Patent No.: US 11,389,497 B2
(45) Date of Patent: Jul. 19, 2022

(54) PHARMACEUTICAL COMPOSITION FOR TREATING CANCER

(71) Applicant: Institute of Advance Sciences, Inc., Dartmouth, MA (US)

(72) Inventors: Bal Ram Singh, Dartmouth, MA (US); Chandra K Mayanil, Naperville, IL (US); Tadanori Tomita, Glenview, IL (US); Raj Kumar, Dartmouth, MA (US)

(73) Assignee: Prime Bio, Inc., North Dartmouth, MA (US)

( * ) Notice: Subject to any disclaimer, the term of this patent is extended or adjusted under 35 U.S.C. 154(b) by 0 days.

(21) Appl. No.: 16/850,190

(22) Filed: Apr. 16, 2020

(65) Prior Publication Data

US 2021/0023158 A1    Jan. 28, 2021

Related U.S. Application Data

(60) Provisional application No. 62/834,879, filed on Apr. 16, 2019.

(51) Int. Cl.
| | | |
|---|---|---|
| *A61K 36/53* | (2006.01) | |
| *A61K 31/375* | (2006.01) | |
| *A61K 31/191* | (2006.01) | |
| *A61K 9/19* | (2006.01) | |
| *A61K 47/38* | (2006.01) | |
| *A61K 47/26* | (2006.01) | |
| *B82Y 5/00* | (2011.01) | |

(52) U.S. Cl.
CPC ............ *A61K 36/53* (2013.01); *A61K 31/191* (2013.01); *A61K 31/375* (2013.01); *A61K 47/26* (2013.01); *A61K 47/38* (2013.01); *A61K 9/19* (2013.01); *B82Y 5/00* (2013.01)

(58) Field of Classification Search
None
See application file for complete search history.

(56) References Cited

U.S. PATENT DOCUMENTS

2003/0185911 A1* 10/2003 Qazi ...................... A61K 36/59
424/729

FOREIGN PATENT DOCUMENTS

IN    201841039156    * 10/2020

OTHER PUBLICATIONS

Utispan et al. (Ethanolic extract of *Ocimum sanctum* leaves reduced invasion and matrix metalloproteinase activity of head and neck cancer cell lines, available online posted Mar. 27, 2019). (Year: 2019).*

* cited by examiner

*Primary Examiner* — Melissa S Mercier

(57) ABSTRACT

Presently claimed invention related to a pharmaceutical composition comprising ascorbic acid caffeoylquinic acid, rosmarinic acid. and glycosyl sulfones obtained from *Ocimum Sanctum* and a process for isolating said composition from *Ocimum Sanctum*. Presently claimed invention also provides a method of treating neural crest derived tumors such as malignant neurofibroma and melanoma.

15 Claims, 19 Drawing Sheets

PHARMACEUTICAL COMPOSITION FOR TREATING CANCER

FIELD OF INVENTION

Presently claimed invention related to a pharmaceutical composition composing ascorbic acid, caffeoylquinic acid, rosmarinic acid, and glycosyl sulfones obtained from *Ocimum Sanctum* and a process for isolating said composition from Sanctum. Presently claimed invention also provides a method of treating neural crest derived tumors such as malignant neurofibroma and melanoma.

BACKGROUND OF INVENTION

*Ocimum Sanctum* (OS), Tulsi an aromatic plant in the family Lamiaceac, Lin, is valued for its versatility in having anti-inflammatory, anti-oxidant, immune-modulatory and anti-stress properties, and more recently for its anti-cancer/tumorigenic properties. The use of Tulsi extracts has never been reported for the treatment of neural crest derived malignant peripheral nerve sheath tumor and melanoma Malignant neurofibromas include peripheral nerve sheath tumors (MPNSTs), which are aggressive soft tissue sarcomas, arising from peripheral nerve sheaths. MPNSTs are also known as "malignant schwannoma" which are a high-grade spindle cell neoplasm [1]. MPNSTs are 5-10% of all soft tissue sarcomas with tumors incidence of 0.001% in the general population, and 8-13% with neurofibromatosis (NF 1) [2, 3]. 50% of all MPNSTs are seen in NF1 patients and a leading cause of mortality in NF1 [4]. NH has an incidence of 1:2500 to 1:3500 with 100% penetrance and variable expressivity MPNSTs occurs mainly in adults (between age 20 and 50 years), although 10-20% may occur in the pediatric population [5-7]. NF1-MPNST arises most frequently in preexisting plexiform neurofibromas. Metastasis is most frequently seen to lung soft tissue, bone. liver, brain, regional lymph nodes, skin, and retroperitoneum. Prognosis in MPNST is poor, especially in those tumors that cannot be fully resected. Compared with other soft tissue sarcomas, MPNSTs have the highest risk of sarcoma specific death [12].

Epigenetic mechanisms have been shown to play a very important role in the neurofibroma progression to a malignant phenotype as MPNST. MPNSTs are characterized by the loss of PRC 2 (Polycomb Repressive Complex), which has histone methyltransferase activity and primarily trimethylates histone H3 on lysine 27 (i.e. H3K27me3). Multiple studies have concluded that loss of PRC2 activity contributes to the development of many types of cancer, including MPNSTs [8-14]. Indeed, the absence of PRC2 activity reduces H3K27me3 at the promoters of genes whose transcriptional repression leads to re-enter the cell cycle, which, in turn, inhibits cell differentiation of SC s (Schwann Cells). This process is called de-differentiation of Schwann cells [15-16]. There is another class of protein complex called the Nucleosome Remodeling Deacetylase (NuRD), which also plays an important role in tumorigenesis of SCs. The NuRD complex comprises of HDAC1/2, GATA2A/2B, MBD2/3, CHD3/4, and MTA 1/2/3, functioning as a chromatin silencing complex [17]. NuRD restricts the expression of key pluripotency genes [18], suggesting that NuRD may suppresses cell pluripotency in NF1-MPNSTs.

Surprisingly it was found that a hydrophilic fraction obtained from *Ocimum Sanctum*, was able to remodel chromatin from the tumorigenic Schwann cell to a differentiated Schwann cell, thereby promoting differentiation of tumorigenic Schwann cells.

SUMMARY OF INVENTION

Accordingly, the first aspect of the presently claimed invention is to provide a pharmaceutical composition comprising ascorbic acid, caffeoylquinic acid, rosmarinic acid, and glycosyl sulfones wherein the pH of the composition is maintained in the range of 5.5 to 8. (Flow sheet of the isolation protocol outlined in FIG. 2).

The second aspect of the presently claimed invention is to provide a process for preparation of bioactive fraction, *Ocimum Sanctum* hydrophilic fraction-I, from plant *Ocimum Sanctum* comprising steps of a) prepare mixture of *Ocimum Sanctum* leaves powder water and boil the mixture for 5 minutes to obtain a boiled mixture;
b) cool the boiled mixture obtained in step a) to room temp and centrifuge at 3000×g for 20 minutes:
c) isolate the supernatant and adjust the pH to 7.2
d) lyophilize the solution obtained in step c) to obtain a powder,
e) suspend the powder obtained in step d) in 80% methanol to obtain a powder-organic solvent mixture,
f) stir the powder-organic solvent mixture obtained in step e) overnight to obtain an organic solvent mixture,
g) centrifuge at 3000× the organic solvent mixture obtained in step f) for 20 minutes to obtain an organic fraction. This is considered as *Ocimum Sanctum* hydrophilic fraction-I or OSHP-1,
h) lyophilize the organic fraction oz3/4ained in step g) to obtain the bioactive fraction in powder form comprising of ascorbic acid, caffeoylquinic acid, rosmarinic acid, and glycosyl sulfones as evident by the HPLC-Mass spectrometric studies (FIGS. 3A and 3B).

The third aspect of the presently claimed invention provide method for the treatment of malignant neurofibroma by administrating suitable amount of the pharmaceutical composition comprising ascorbic acid, caffeoylquinic acid. rosmarinic acid, and glycosyl sulfones wherein the pH of the composition is maintained in the range of 5.5 to 8.

DETAILED DESCRIPTION OF THE INVENTION

Figure 1:
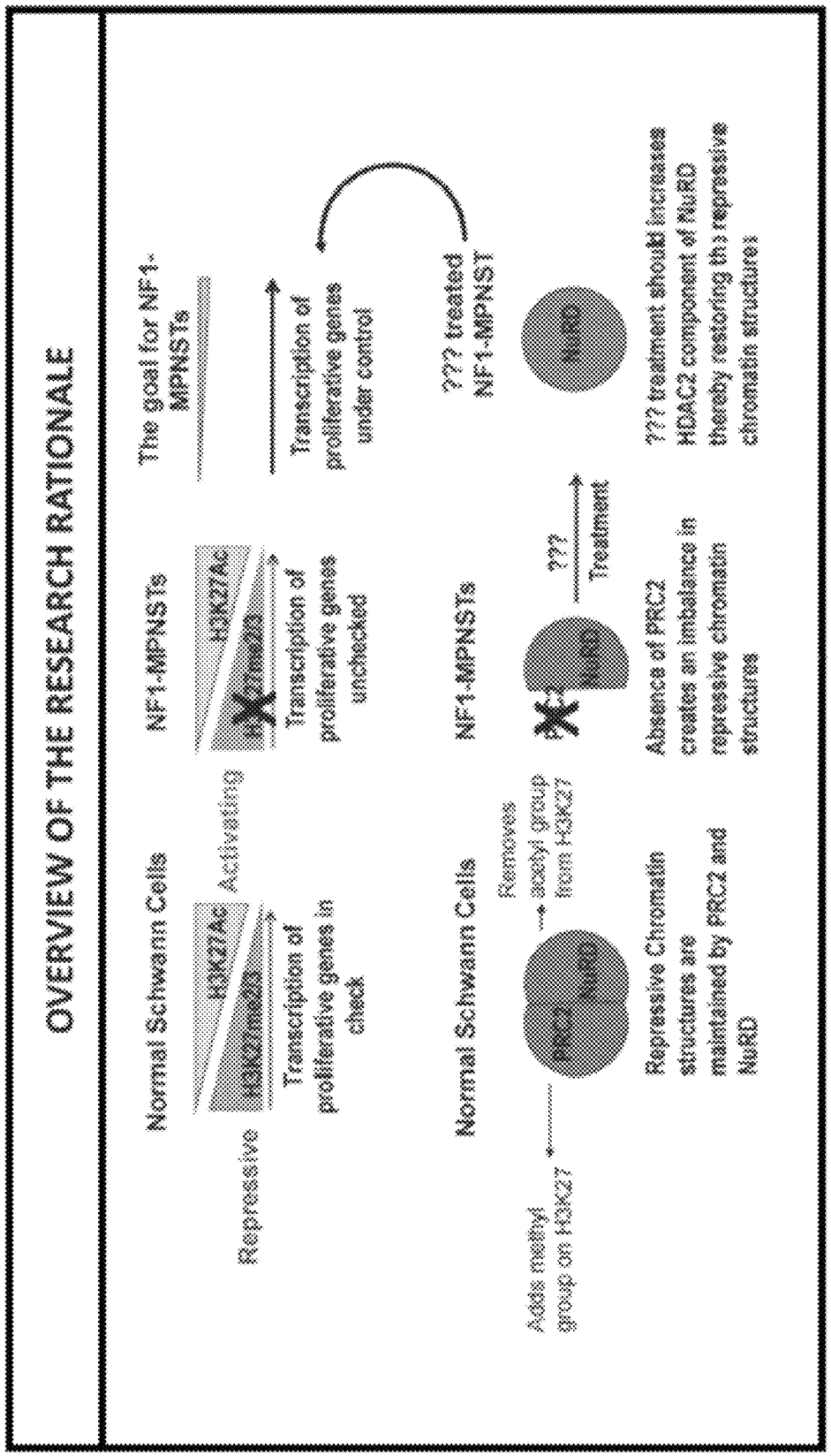
FIG. 1 illustrates an overview of the entire research, in accordance with an exemplary embodiment of the present disclosure. An overview of the Research Rationale The normal Schwann Cells has H3K27Ac (an activating chromatin) as well as H3K27me2/3 (a repressive chromatin) in perfect balance. This balance between the methylation and acetylation of H3K27 is maintained by polycomb remodeling complex (PRC2), which is a methyl transferase enzyme complex responsible for adding the methyl group on H3K27 and Nucleosome Remodeling Deacetylase complex (NuRD complex) responsible for removing the acetyl group from 113K27. In NFI-MPNSTs an imbalance between the acetylation and methylation ratio of H3K27 occurs because in NFI associated MPNSTs there is a loss of fraction mutation in PRC which renders the chromatin devoid of H3K27 methylation. This leads to H3K27Ac which drives overexpression of tumorigenic/cancer genes. The goal which we wanted to pursue was to up-regulate the repressive chromatin so that there is a decrease in H3K27Ac and therefore reduced expression of tumorigenic/cancer genes. We were able to achieve our objective by OSHP-1 treatment in ST88-14 cells (NF-I related MPNST).

Before the present compositions and formulations of the presently claimed invention are described, it is to be understood that this invention is not limited to particular compositions and formulations described, since such compositions and formulation may, of course, vary with its use—treat indications and tissues involved. It is also to be understood that the terminology used herein is not intended to be limiting, since the scope of the presently claimed invention will be limited only by the appended claims.

In first embodiment the presently claimed invention 1 s directed to a pharmaceutical composition comprising:
i. ascorbic acid,
ii. caffeoylquinic acid,
iii. rosmarinic acid, and
iv. glycosyl sulfones
wherein the pH of the composition is maintained in the range of 5.5 to 8.

In another preferred embodiment the presently claimed invention is directed a pharmaceutical composition comprising
i. ascorbic acid,
ii. caffeoylquinic acid,
iii. rosmarinic acid, and
iv. glycosyl sulfones
wherein the pH of the composition is maintained in the range of 7 to 7.4.

In another embodiment the presently claimed invention is directed to a pharmaceutical composition, wherein the weight ratio of
i. ascorbic acid,
ii. caffeoylquinic acid,
iii. rosmarinic acid, and
iv. glycosyl sulfones.
is the range of 0.8:1.2; 2:5; 0.6:1; and 2:2.6 respectively.

Still another embodiment of the present claimed invention is directed to a pharmaceutical composition, wherein the weight ratio of the
i. ascorbic acid,
ii. caffeoylquinic acid,
iii. rosmarinic acid, and
iv. glycosyl sulfones
is in the range of 0.9:1.1; 2:5; 0.7:1; and 2:2.6 respectively.

In another embodiment the pharmaceutical composition further comprises pharmaceutically acceptable carrier, diluent, and additives.

In a preferred embodiment the pharmaceutically acceptable carrier is selected from the group consisting of microsphere nanotubes nanoparticles, nanofibers peptide analogues, any other pharmaceutically acceptable carriers for delivery, and/or any combination of these delivery methods. Yet another embodiment of the present claimed invention. the selected from the group consisting of lactose, mannitol, sorbitol, microcrystalline cellulose, sucrose, sodium citrate, di-calcium phosphate or mixture thereof.

In another preferred embodiment the additives are selected from the group consisting of glycols (such as PEGS), Hyaluronic acid (ar sodium hyaluronate), and surface-active agents (such as polysorbates).

In an embodiment of the present claimed invention is directed to a process for preparation of bioactive fraction, *Ocimum Sanctum* jn hydrophilic fraction-1, from plant *Ocimum Sanctum* comprising steps of
a) preparing mixture of *Ocimum Sanctum* in water, wherein a ratio of *Ocimum Sanctum* to water is 1:100, and wherein the *Ocimum Sanctum* is in a powder form, and boiling the mixture for a predetermined time to obtain a boiled mixture;
b) cooling the boiled mixture to a room temperature and centrifuged at 3000×g for a predetermined time minutes to obtain a supernatant;
c) isolating the supernatant and adjusting the pH of the supernatant in a range of 6.8 to 7.6 to obtain a solution;
d) lyophilizing the solution to obtain a powder;
e) suspending the powder in 80% methanol to obtain a powder-organic solvent mixture;
f) stirring the powder-organic solvent mixture for a predetermined duration to obtain an organic solvent mixture;
g) centrifuging at 3000×g the powder-organic solvent mixture for a predetermined time to obtain an organic fraction; and
h) lyophilizing the organic fraction to obtain the bioactive fraction in powder form comprising in the weight ratio:
i. ascorbic acid is in a range of about 0.8 to 1.2,
ii. caffeoylquinic acid is in a range of about 2 to 5,
iii. rosmarinic acid is in a range of about 0.6 to 1, and
iv. glycosyl sulfones is in a range of about 2 to 2.6.

Yet another embodiment of the presently claimed invention is directed to a process for preparation of bioactive fraction, *Ocimum Sanctum* hydrophilic fraction (OSHP-1) from plant *Ocimum Sanctum* comprising steps of:
a) preparing mixture of *Ocimum Sanctum* in water, wherein a ratio of *Ocimum Sanctum* to water is 1:100, and wherein the *Ocimum Sanctum* is in a powder form, and boiling the mixture for a predetermined time to obtain a boiled mixture;
b) cooling the boiled mixture to a room temperature and centrifuged at 3000×g for a predetermined time minutes to obtain a supernatant;
c) isolating the supernatant and adjusting the pH of the supernatant in a range of 6.8 to 7.6 to obtain a solution;
d) lyophilizing the solution to obtain a powder;
e) suspending the powder in 80% methanol to obtain a powder-organic solvent mixture;
f) stirring the powder-organic solvent mixture for a predetermined duration to obtain an organic solvent mixture;
g) centrifuging at 3000×g the powder-organic solvent mixture for a predetermined time to obtain an organic fraction; and.
h) lyophilizing the organic fraction to obtain the bioactive fraction in powder form comprising in the weight ratio:
i. ascorbic acid is in a range of about 0.9:1.1,
ii. caffeoylquinic acid is in a range of about 2:5,
iii. rosmarinic acid is in a range of about 0.7:1, and
iv. glycosyl sulfones is in a range of about 2:2.6.

In another embodiment the *Ocimum Sanctum* leaves powder is dried leaf powder.

In another embodiment the pH of the solution is 7.2.

In another preferred embodiment the pH of the solution is adjusted to 7 to 7.4.

In another preferred embodiment the organic solvent in step e) is selected from the group consisting of alcoholic solvents and ether solvents.

Yet another embodiment the solvent is selected from the group consisting of methanol, ethanol, 1-propanol, 2-propanol, cyclohexanol, methyl cyclohexanol.

Still another preferred embodiment the alcoholic solvent is methanol.

In another preferred embodiment the ether solvent is selected from the group consisting of dimethyl ether, diethyl ether, ethyl methyl ether, ether, tetrahydrofuran.

In another preferred embodiment the powder obtained in step g) is further dissolved in an alcoholic solvent, wherein the alcoholic solvent is selected from the group consisting of methanol, ethanol, 1-propanol, 2-propanol, cyclohexanol, methyl cyclohexanol.

In another preferred embodiment the mixture will be used as a liquid or solid formulation.

In an embodiment presently claimed invention directed to a method for the treatment of malignant neurofibroma.

In another preferred embodiment the malignant neurofibroma is peripheral nerve sheath tumors and other neural crest cell-derived tumors having a lineage from neural crest: melanocytic tumors, peripheral neuroblastic tumors, embryonal tumors of the CNS including 10 medulloblastoma, atypical teratoid/rhabdoid tumor and CNS/supratentorial primitive neuroectodermal tumors, paraganglioma and other tumors of neural crest origin (medullary thyroid carcinoma)

In another preferred embodiment the wherein method of administration is oral route. sublingual and buccal routes, rectal route, vaginal route, ocular route, optic route or nasal route, and topical route OSHP-1 can be used to treat one of the severest forms of MPNST, which has NF1 as well as SUZ12 (polycomb repressive complex 2 or PRC 2 component) loss of function mutation. OSHP-1 compensates for the loss PRC2 repressive chromatin by a reciprocal increase in the 20 activity of nucleosome remodeling deacetylase or NuRD complex and stops cell proliferation, causing differentiation of undifferentiated Schwann cells.

OSHP-1 can treat MPNST associated NF1 rather than treat the symptoms. The kinds of MPNSTs on which the OSHP-1 works are the ones showing NF1 and PRC2 loss of function mutation as described in the overview of research (see below).

The types of patients with malignant peripheral nerve sheath tumors (MPNSTs) showing NF1 and PRC2 loss-of-function mutation, and possibly glioma NF1 patients who are at risk of developing cancerous tumors that grow along nerves. These tumors, which usually develop in adolescence or adulthood, are called malignant peripheral nerve sheath tumors (MPNS'Ts). People with NF1 also have an increased risk of developing other cancers including brain tumors and leukemia. OSHP-1 is potentially capable of treating this.

Secondly, the invention is potentially capable to treat the pediatric patients who developed benign growths called Lisch nodules which appear in the colored part of the eye (the iris). Affected individuals may develop tumors that grow along the nerve leading from the eye to the brain (the optic nerve). These tumors, which are called optic gliomas, may lead to reduced vision or total vision loss.

The pharmaceutical composition and the bio extracts are potentially capable of treating the cancerous tumors that grow along the nerves as well as optic glioma in NF patients.

The overview of our invention: In MPNST there is a significant loss of repressive chromatin, because of which the genes which should not get expressed are aberrantly expressed and produce tumors in peripheral as well as in the central nervous system. Therefore, our goal was to increase the levels of repressive chromatin, so that cell proliferation can be differentiation of these tumors can be achieved (FIG. 1).

Figure 2:
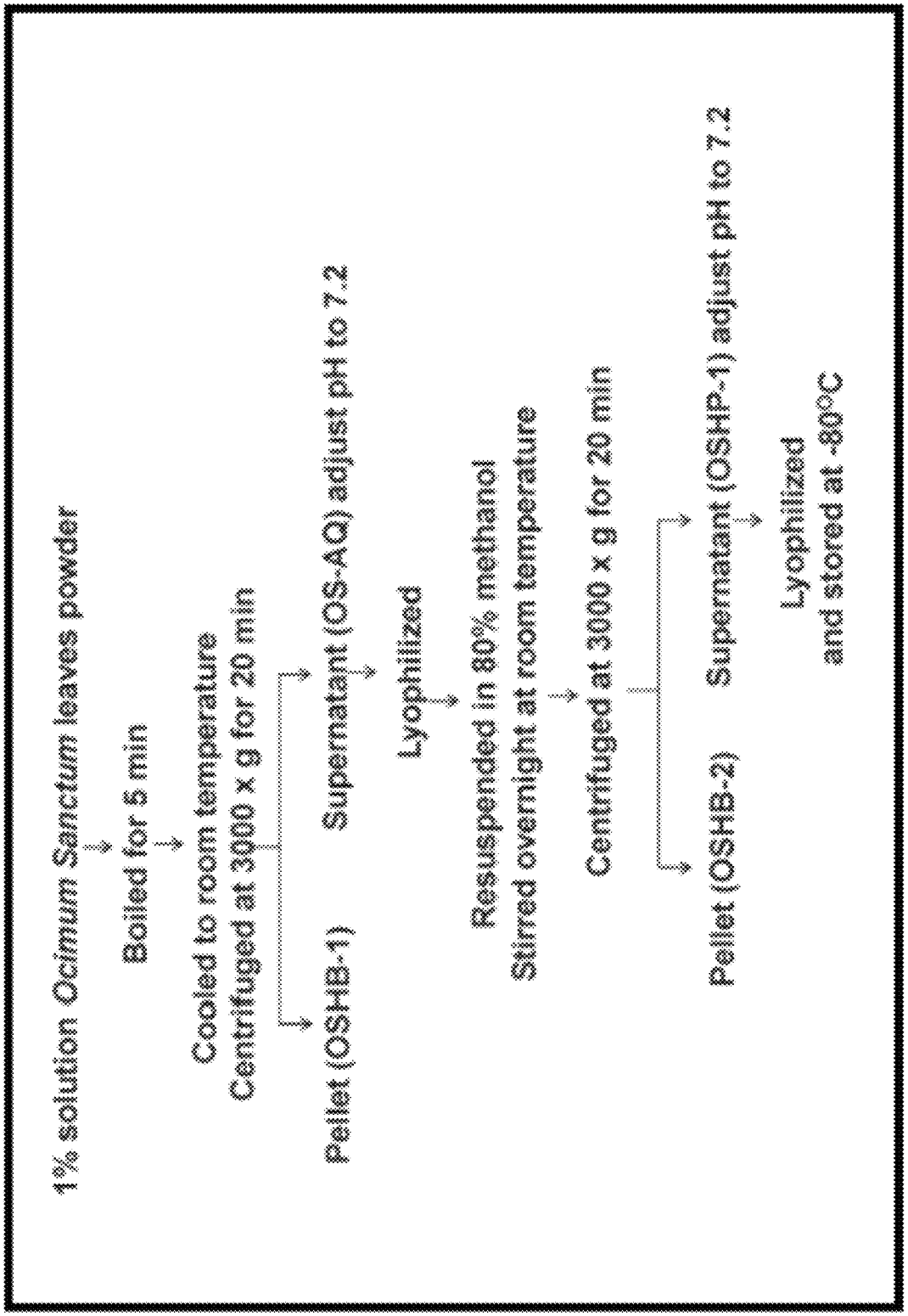
FIG. 2 illustrates schematic for isolation of OSHP-1 from *Ocimum Sanctum* leaves powder, in accordance with an exemplary embodiment of the present disclosure.
Figure 3A:
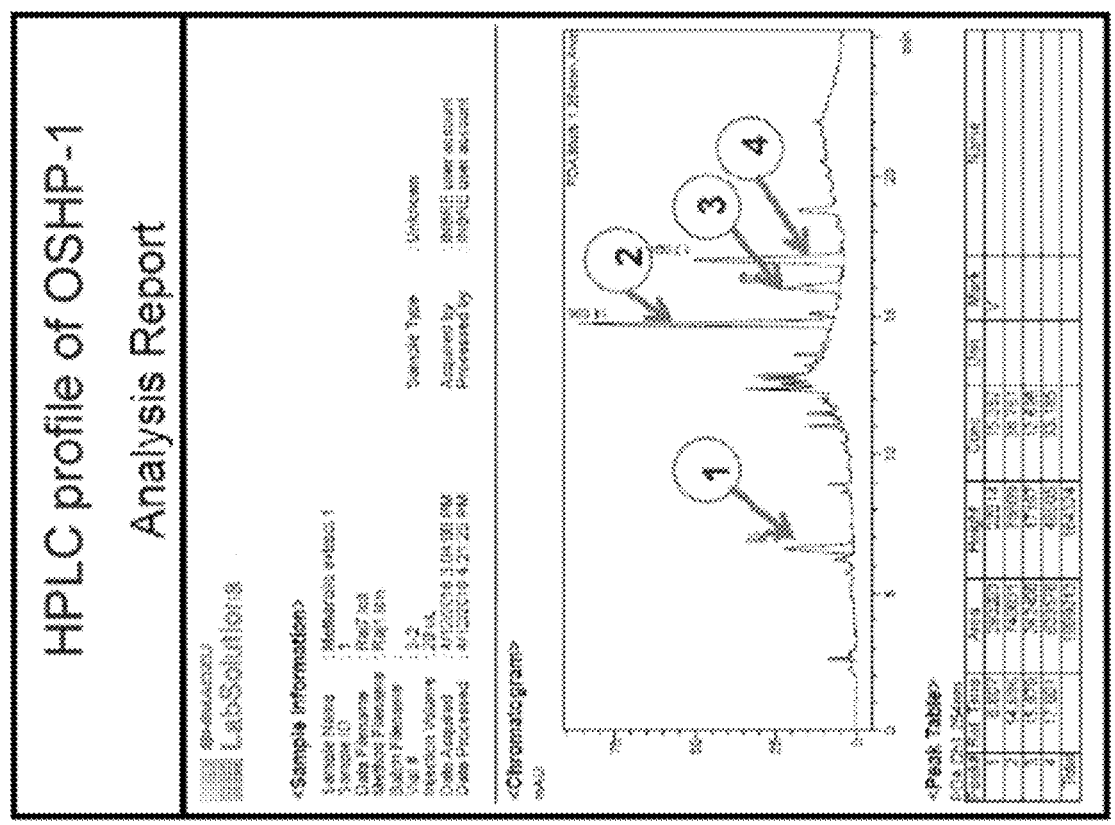
FIG. 3A illustrates an analysis report of HPLC chromatogram showing major compounds in the methanolic extract at retention Time (RT) 6.607, 14.696, 15.979 and 17.001 min, in accordance with an exemplary embodiment of the present disclosure.
Figure 3B:
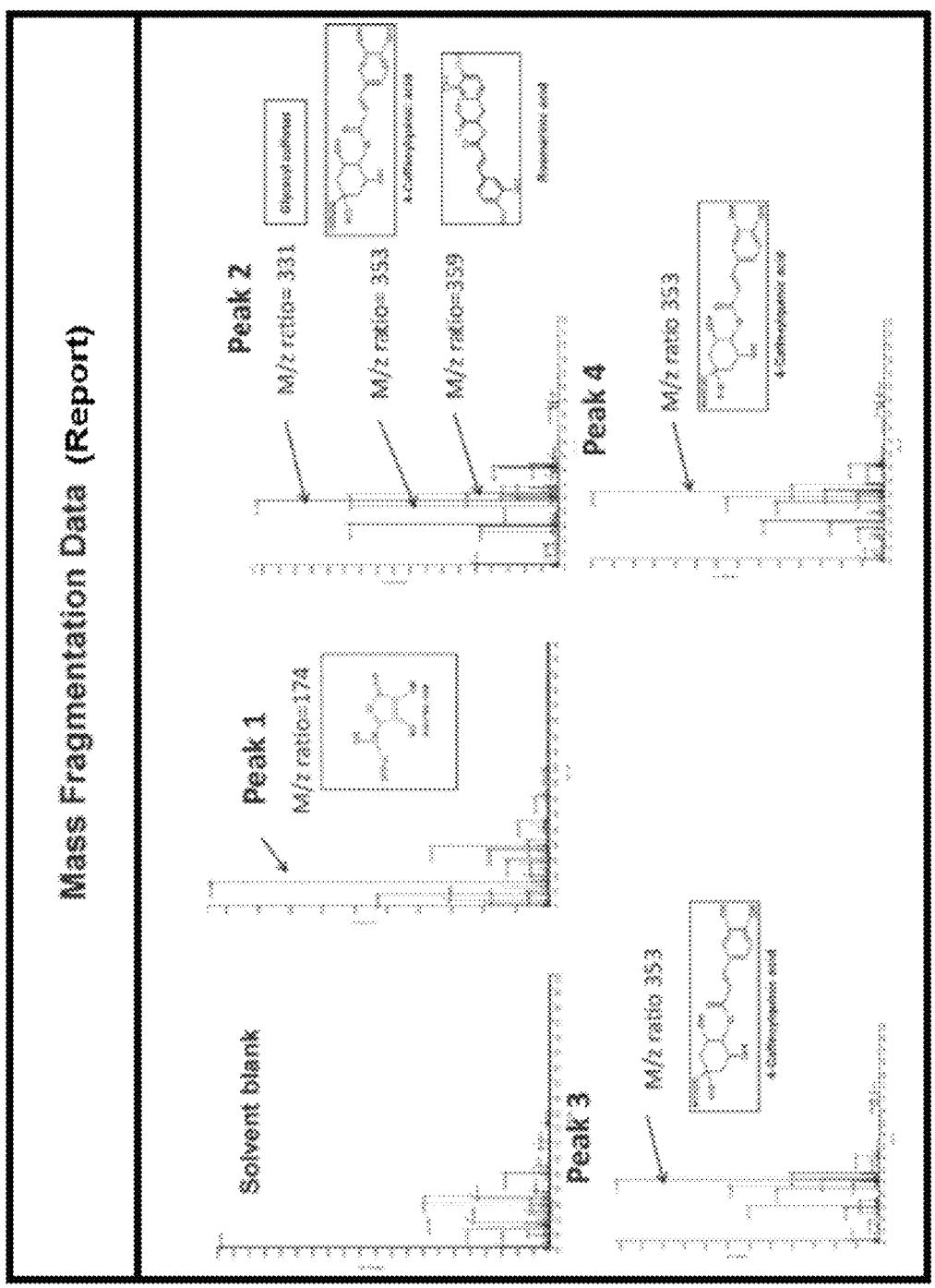
FIG. 3B illustrates a report showing mass spectrometry (MS 1) and molecular defragmentation data depicting various HPLC Peaks, in accordance with an exemplary embodiment of the present disclosure. The report showing mass spectrometry (MS 1) and molecular defragmentation data reveal that HPLC Peak I with M/z ratio 174.969 (major fragment) and a possible derivative of ascorbic acid. HPLC Peak 2, 3 and 4 with M/z 353.266 (major fragment) and representing either the caffeoylquinic acid (M/z of 353) or isomer of rosmarinic acid (M/z ratio 359.316).

Characterization of OSHP-1: OSHP-1 was extracted as described in FIG. 2 and characterized by HPLC-Mass Spectrometric analysis (FIG. 3A and FIG. 3B). OSHP-1 showed 4 HPLC peaks at retention time (RT) 6 607, 14.696, 15.979 and 17.001 min. Mass spectrometry (MS) and molecular defragmentation data reveal that HPLC Peak I with M/z ratio 174.969 (major fragment) could be ascorbic acid or a derivative of ascorbic acid. HPLC Peak 2, 3 and 4 with M/z 353.266 (major fragment) could be caffeoylquinic acid (M/z of 353) and rosmarinic acid (M/z ratio 359.316) or isomer of caffeoylquinic and rosmarinic acid (FIGS. 3A and 3B).

Figure 4:
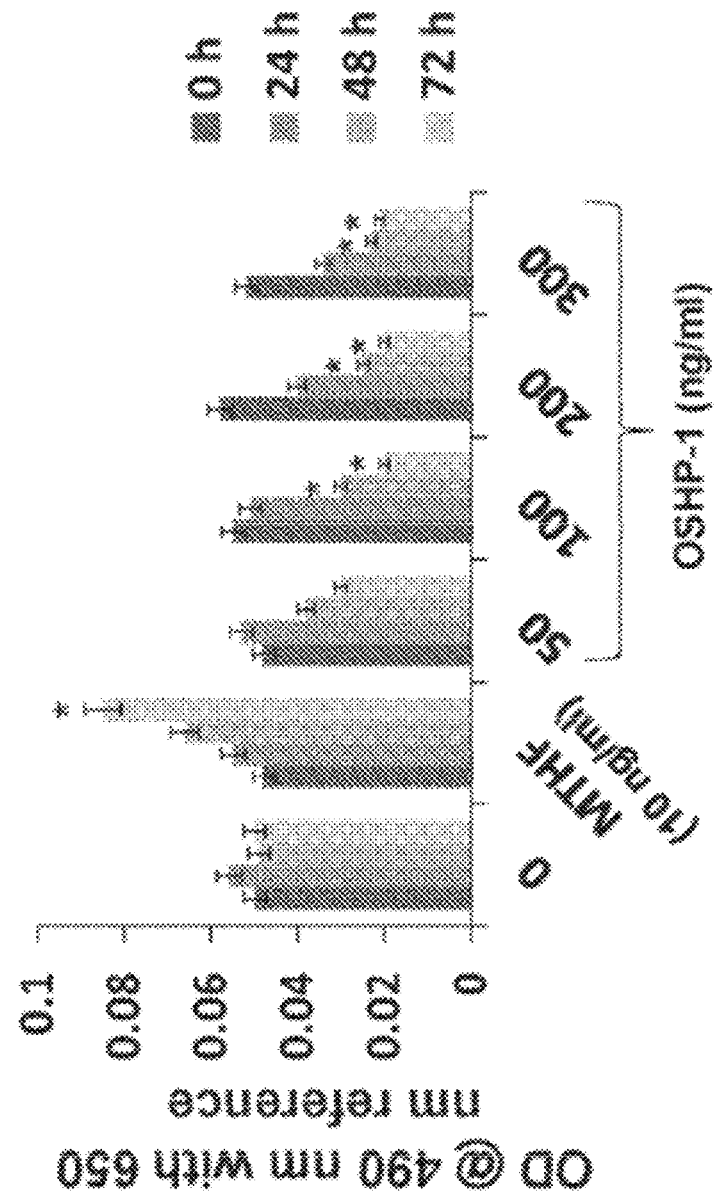
FIG. 4 illustrates a report on cell Viability Assays using the MTS Assay Kit (Colorimetric) (ab 197010) Cell proliferation, in accordance with an exemplary embodiment of the present disclosure. As shown, viability and cytotoxicity was assessed on cells. Cells were treated with the appropriate concentrations of OSHP-1 for 24, 48 and 72 h.

Effect of OSHP-1 on Cell proliferation: We performed MTS assays using cells and treated with increasing concentrations of OSHP-1 (50-300 ng/ml) for 0-72 h. The results showed that OSHP-1 inhibited the viability and proliferation of ST88-14 cells in a dose and time dependent manner. Methyl tetra hydro folate (MTHF) increases the cell proliferation was used as a positive control (FIG. 4).

Figure 5A:
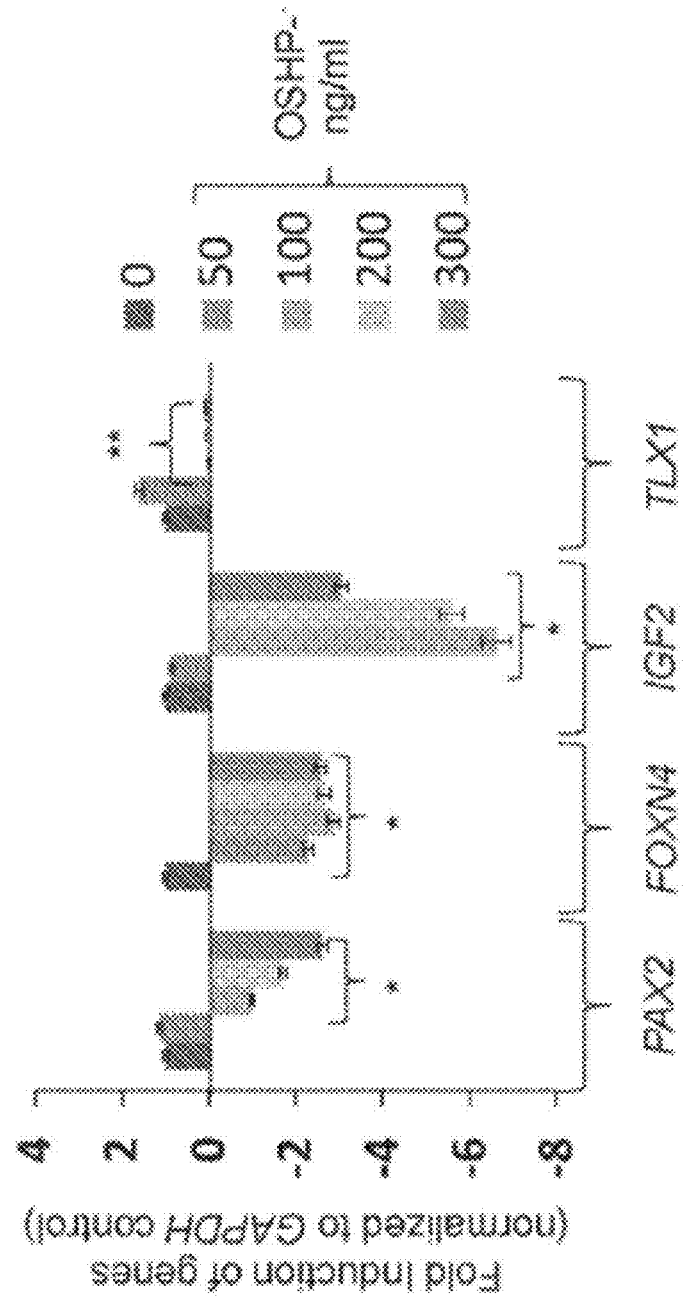
FIG. 5A illustrates a report on real-time quantitative PCR data showing that OSHP-1 reduced the expression of overexpressed genes in ST88-14 cells in accordance with an exemplary embodiment of the present disclosure. Total RNA was isolated using Triazole method. cDNA was synthesized reverse transcriptase and 10 ng of cDNA used for quantitative PCR, (A) The data showed FAX2, FOXN4, IGF2 and TLXI expression was down regulated by OSHP-1 treatment in a dose dependent manner.
Figure 5B:
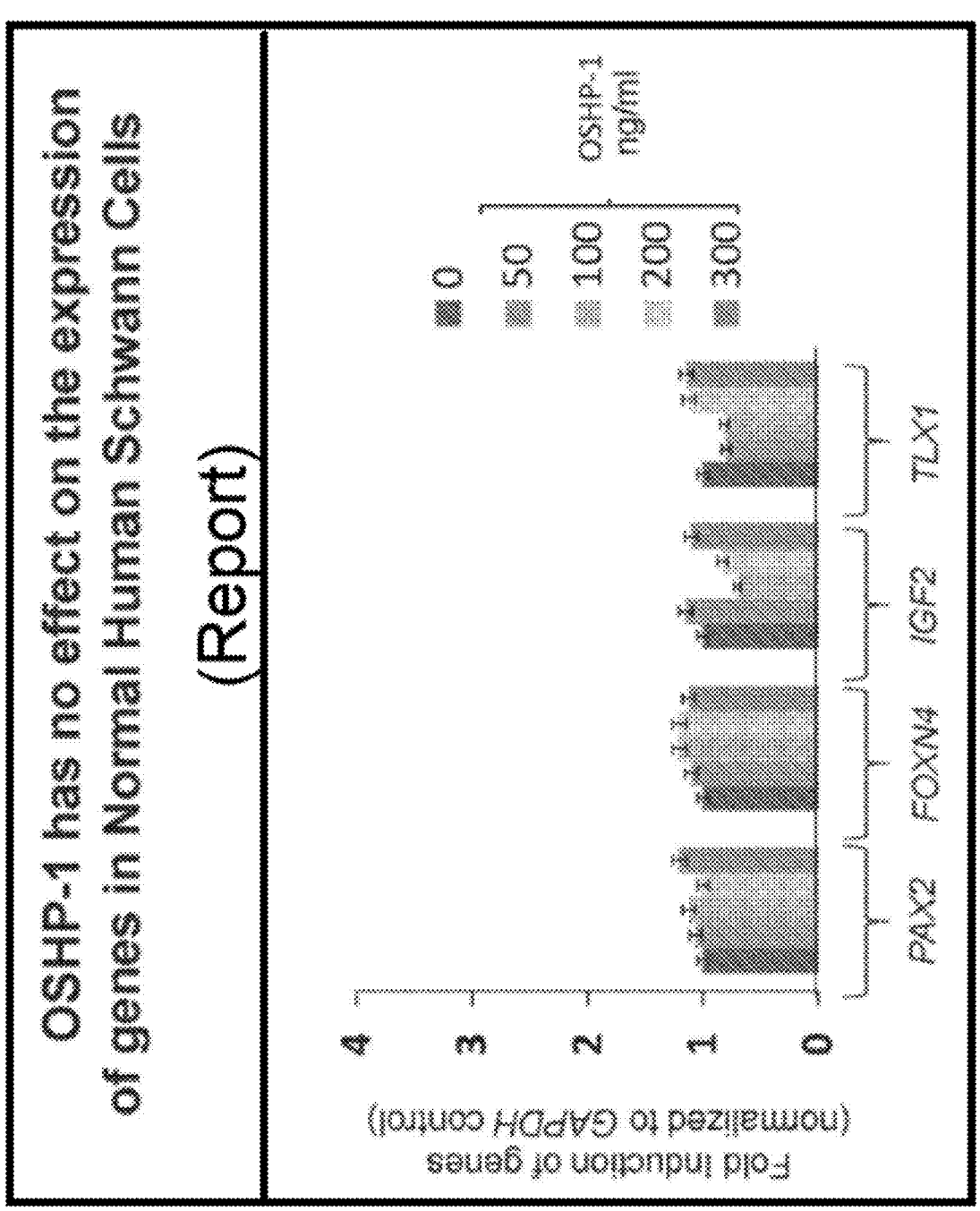
FIG. 5B illustrates, on the contrary, a report on the expression of these genes remain unaffected by OSHP-1 treatment in normal human Schwann Cells, in accordance with an exemplary embodiment of the present disclosure.

Effect of OSHP-1 on the expression of tumorigenic genes. To ascertain whether OSHP-1 decreased the proliferation of ST 88-14 cells, by decreasing the expression of tumorigenic genes, total RNA was isolated from the ST88-14 cells as well as normal Human Schwann cells treated with varying concentrations of OSHP-1 (for 48 h) mentioned above. The RNA was reverse transcribed to cDNA and subjected to quantitative PCR using reverse and forward primers of FAX2, FOXN4, IGF2 TLXI genes (Lee et 2014), and was normalized by the expression of GAPDH (FIG. 5A). Neither OSHP-1 nor its individual components had any effect on the expression of these genes. Overall the data indicate that OSHP-1 decreased the expression of tumorigenic genes differentially in cells but not in normal Schwann cells, suggesting that only affects the tumorigenic MPNST cells and not, the normal Schwann cells (FIG. 5B).

Figure 5C:
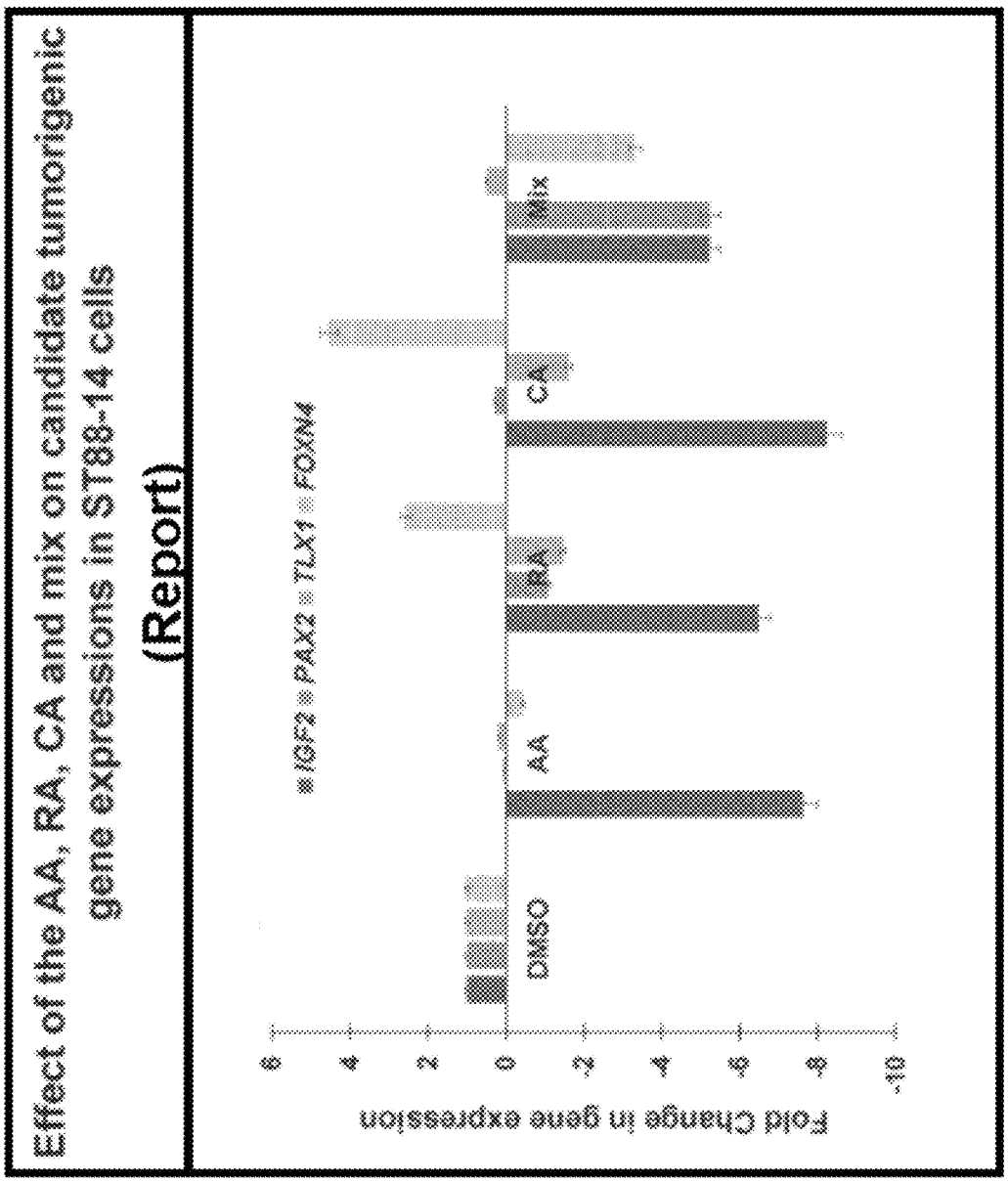
FIG. 5C illustrates a report on effect of AA, RA, CA and mixture of AA+RA+CA on candidate tumorigenic gene expression in ST88-14 cells, in accordance with an exemplary embodiment of the present disclosure.
Figure 5D:
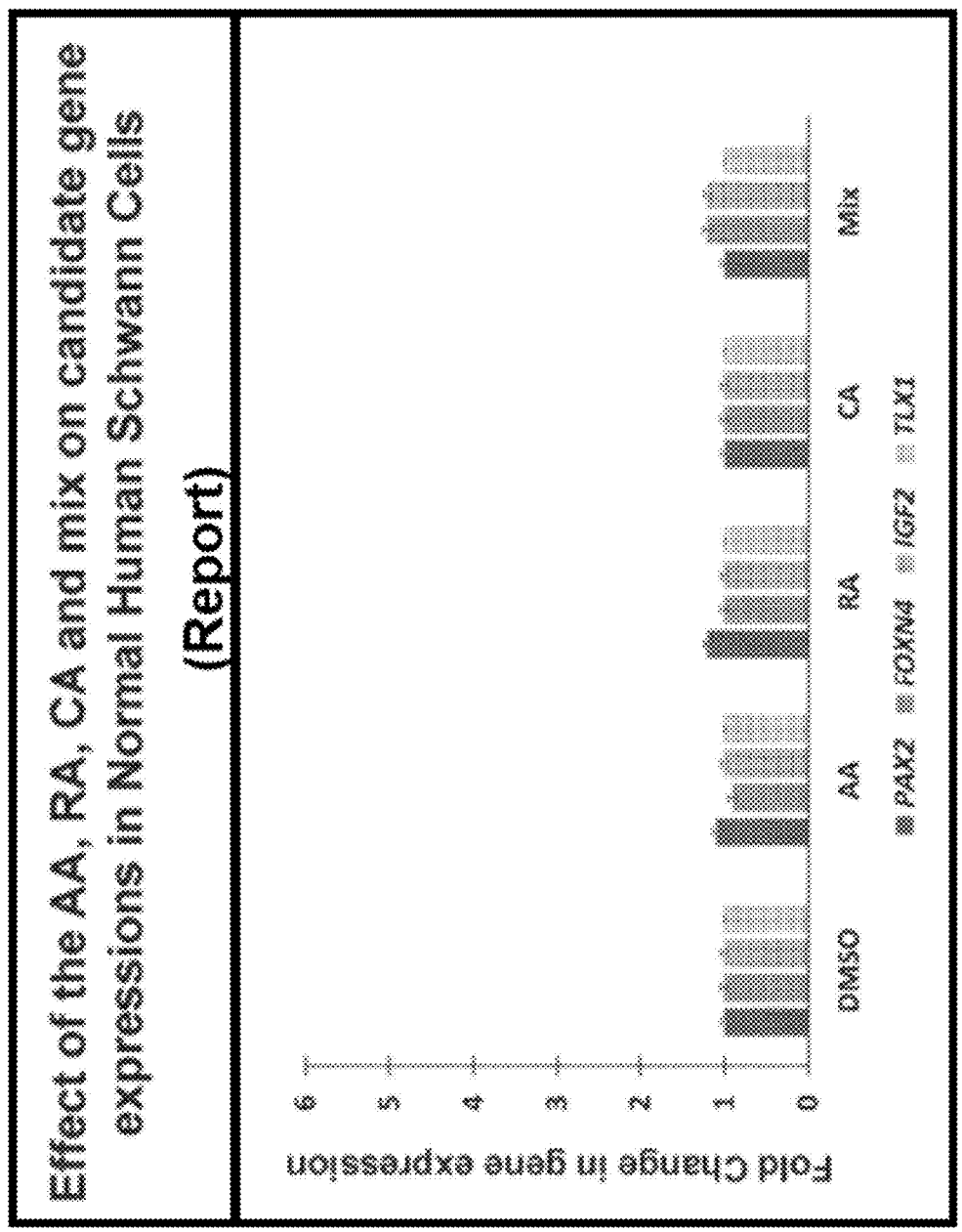
FIG. 5D illustrates a report on effect of the AA RA, CA and mix a candidate gene expression in Normal Human Schwann Cells, in accordance with an exemplary embodiment of the present disclosure.

To ascertain whether the individual compounds ascorbic acid (AA), rosmarinic (IRA) and caffeoylquinic acid (CA) within OSHP-1, decreased the proliferation of ST88-14 cells by decreasing the expression of tumorigenic genes, total RNA was isolated from the ST88-14 and normal human Schwann cells treated with AA, RA, CA and mixture of three compounds (for 48 h), and RT-PCR performed using forward and reverse primers of FAX2, FOXN4, IGF2 and TLXI. The data was normalized by the expression of GAPDH (FIGS. 5C and 5D) and OSHP-1 reversed the expression of certain actively transcribed genes PAX2, FOXN4, IGF2 and TLXI in NF1-MPNST (FIGS. 5C and 5D). The Real Time-Quantitative PCR data show that the genes that are down-regulated in NF1-MPNSTs are down-regulated in a differential manner by AA, RA and CA AA down-regulated IGF2, PAX2 and TLX2 but not FOXN4; RA down-regulated IGF2, FAX2 and TLX2; CA down-regulated IGF2, FAX2 and FOXN4 but not TLX2.

Figure 6A:
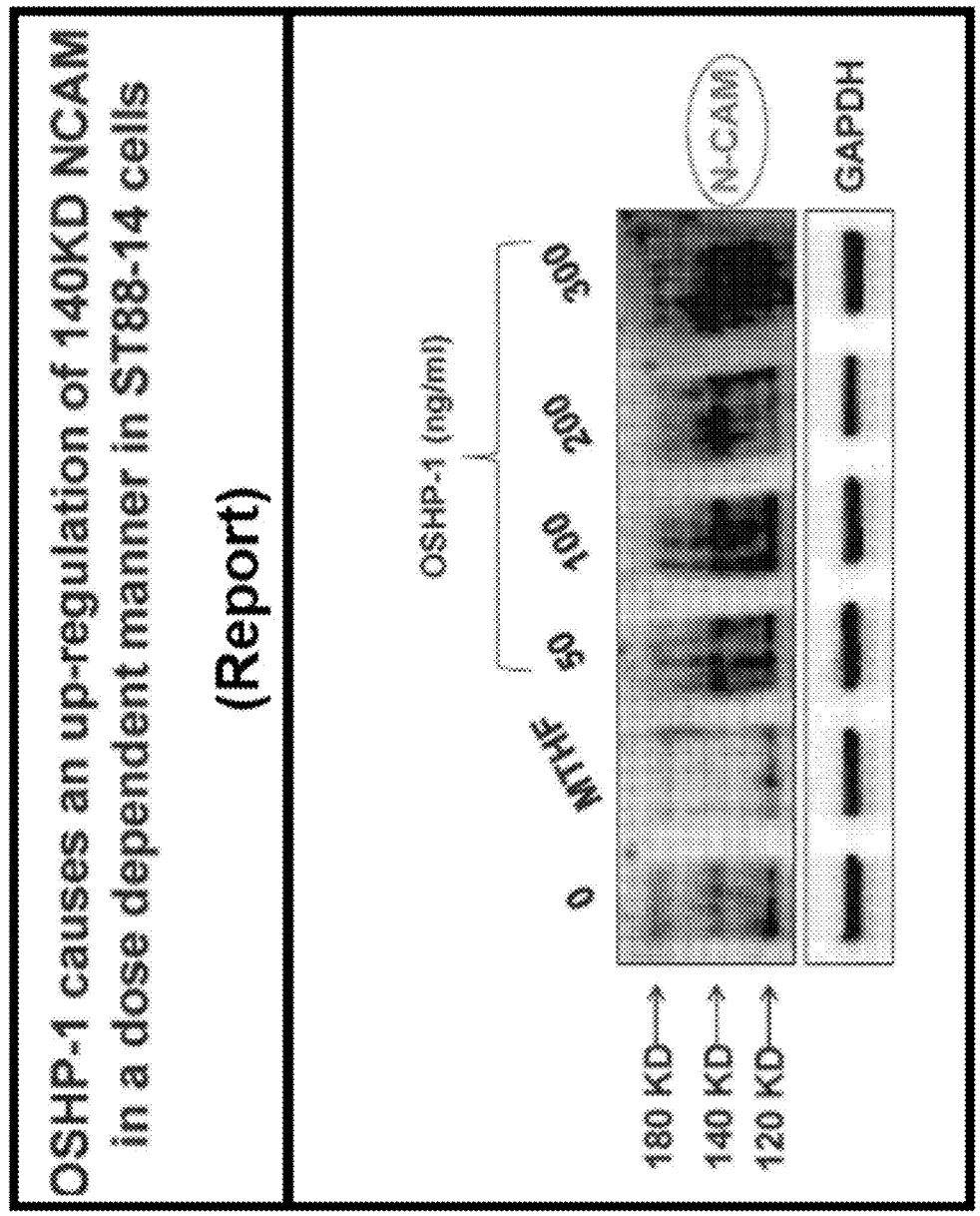
FIG. 6A illustrates a report on effect of OSHP-1 on the expression of different markers, such as ST88-14 cells treated with OSHP-1 with vehicle (zero) or with 5-methyl tetra hydro folate (MTHF) as a negative control or OSHP-1 (50-300 ng/ml) for 48 h, in accordance with an exemplary embodiment of the present disclosure. The total cell lysate was made in RIPA buffer and 20 μg proteins were loaded per well and immunoblotted using NCAM mouse monoclonal antibody (NCAM Antibody-ERIC I:sc-106). The data shows that OSHP-1 treatment caused a dose dependent in the N-CAM 140 KD expression ST88-14, whereas MTHF which is known to up-regulate cell proliferation show a decrease in NCAM expression, suggesting that OSHP-1 treatment causes re-differentiation of the MPNST cells.

Effect of on the expression of marker of differentiation: Neural Cell Adhesion Molecule (N-CAM) is a marker of differentiated Schwann cells. To ascertain whether OSHP-1 can cause the de-differentiated ST88-14 cells to become differentiated, we treated these cells with vehicle (zero) or with tetra hydro folate (MTHF) as a negative control or OSHP-1 (50-300 ng/ml) for 48 h. The total cell lysate was made in RIPA buffer and 20 µg proteins were loaded per well and immunoblotted using NCAM mouse monoclonal antibody (NCAM Antibody-ERIC 1: SC-106). The data shows that OSHP-1 treatment caused a dose dependent increase in the N-CAM 140 KD expression in ST88-14 cells, whereas MTHF which is known to up-regulate cell proliferation [20] show a decrease in NCAM expression, suggesting that OSHP-1 treatment causes re-differentiation of the MPNST cells (FIG. 6A).

Figure 6B:
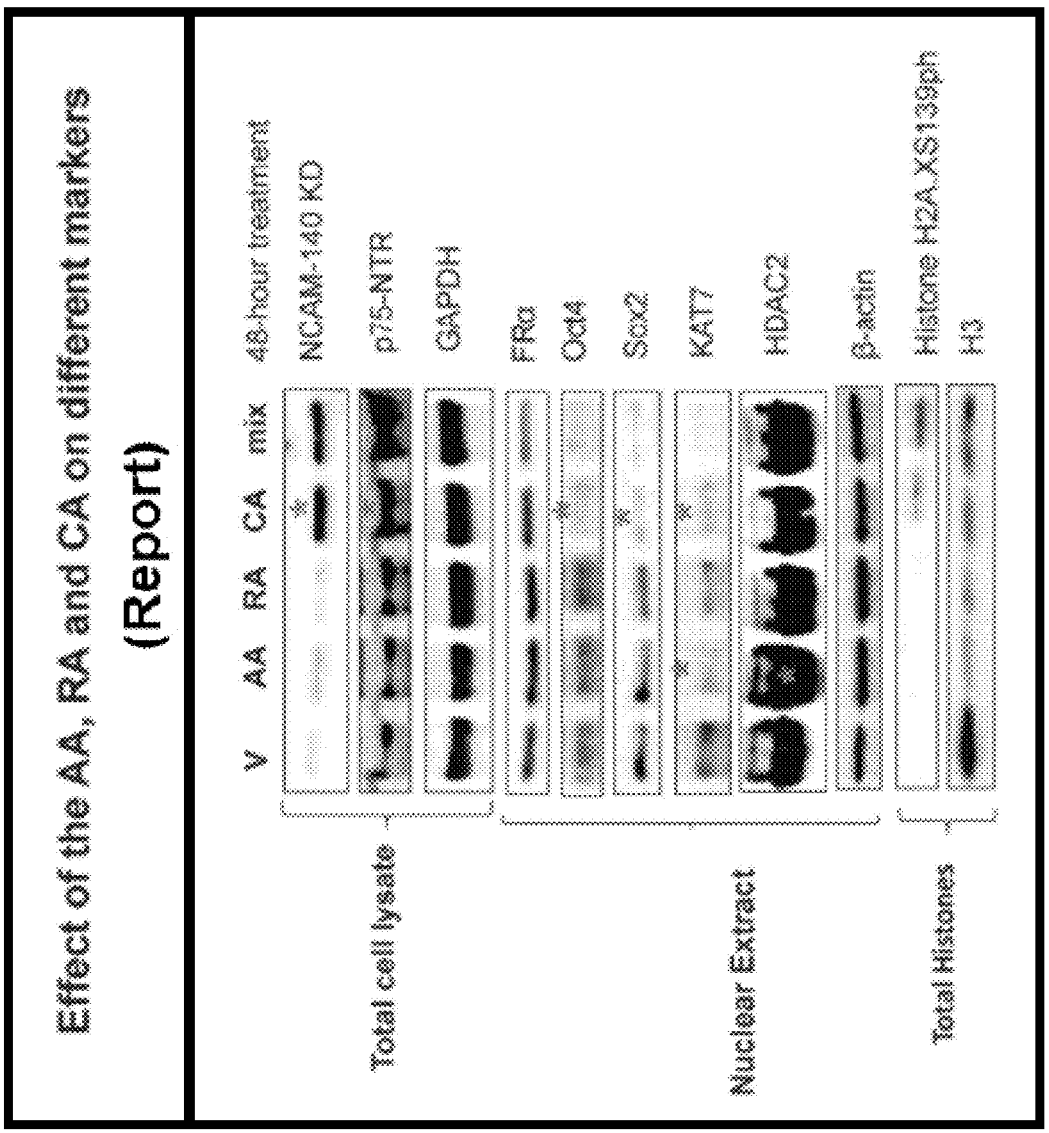
FIG. 6B illustrates a report on the effects of active individual ingredients in OSHP-1 on the expression of different markers, in accordance with an exemplary embodiment of the present disclosure. Amongst the active ingredients in OSHP-1, caffeoylquinic acid was the only one which showed an increase in the expression of N-CAM. Additionally, the expression of another differentiation marker p75 was also increased. Caffeoylquinic acid not only promoted differentiation but it decreased the expression of SOX2, OCT4 and FR-alpha suggesting that the mixture is not only promoting differentiation but also decreases the neural crest cell markers. Additionally, total histone isolated from caffeoylquinic acid treated cells (dead cells as well as live cells) showed that CA causes an increase in the phosphorylation of H2A.X SI 39ph, suggesting that it can function in DNA repair in human MPNST cell line ST88-14.

The effects of active individual ingredients in OSHP-1 on the expression of NCAM: Amongst the active ingredients in OSHP-1 caffeoylquinic acid was the only one which showed an increase the expression of NCAM following treatment. Additionally, the expression of another differentiation marker p75 was also increased caffeoylquinic acid not only promoted differentiation but it decreased the expression of SOX2, OCT4, and FR-alpha, suggesting that the mixture is not only promoting differentiation but also decreases the neural crest cell markers (FIG. 6B). Additionally, total histone isolated from caffeoylquinic acid treated cells (dead cells as well as live cells) showed that CA causes an increase in the phosphorylation of H2A.X SI39ph, suggesting that it can function in DNA repair in MPNST cell line ST88-14 (FIG. 6B).

Figure 7A:
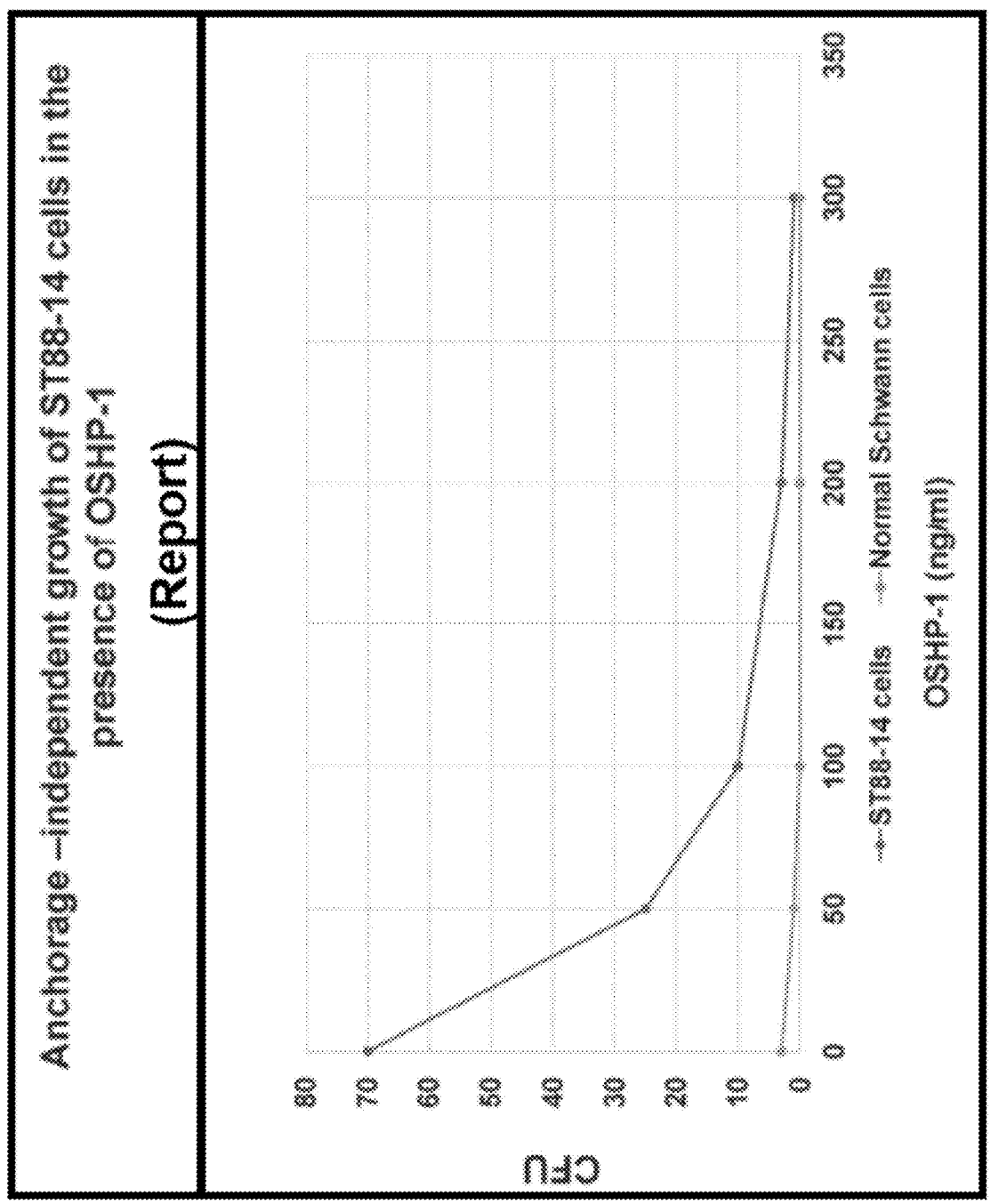
FIG. 7A illustrates a report on effect of OSHP-1 on anchorage independent growth or metastasis, in accordance with an exemplary embodiment of the present disclosure: To determine whether OSHP-1 and its individual components can block the anchorage independent growth of ST88-14 cells, and Normal Human Schwann Cells, by subjecting the cells to Soft Agar colony formation assays the absence and presence of (A) OSHP-1.
Figure 7B:
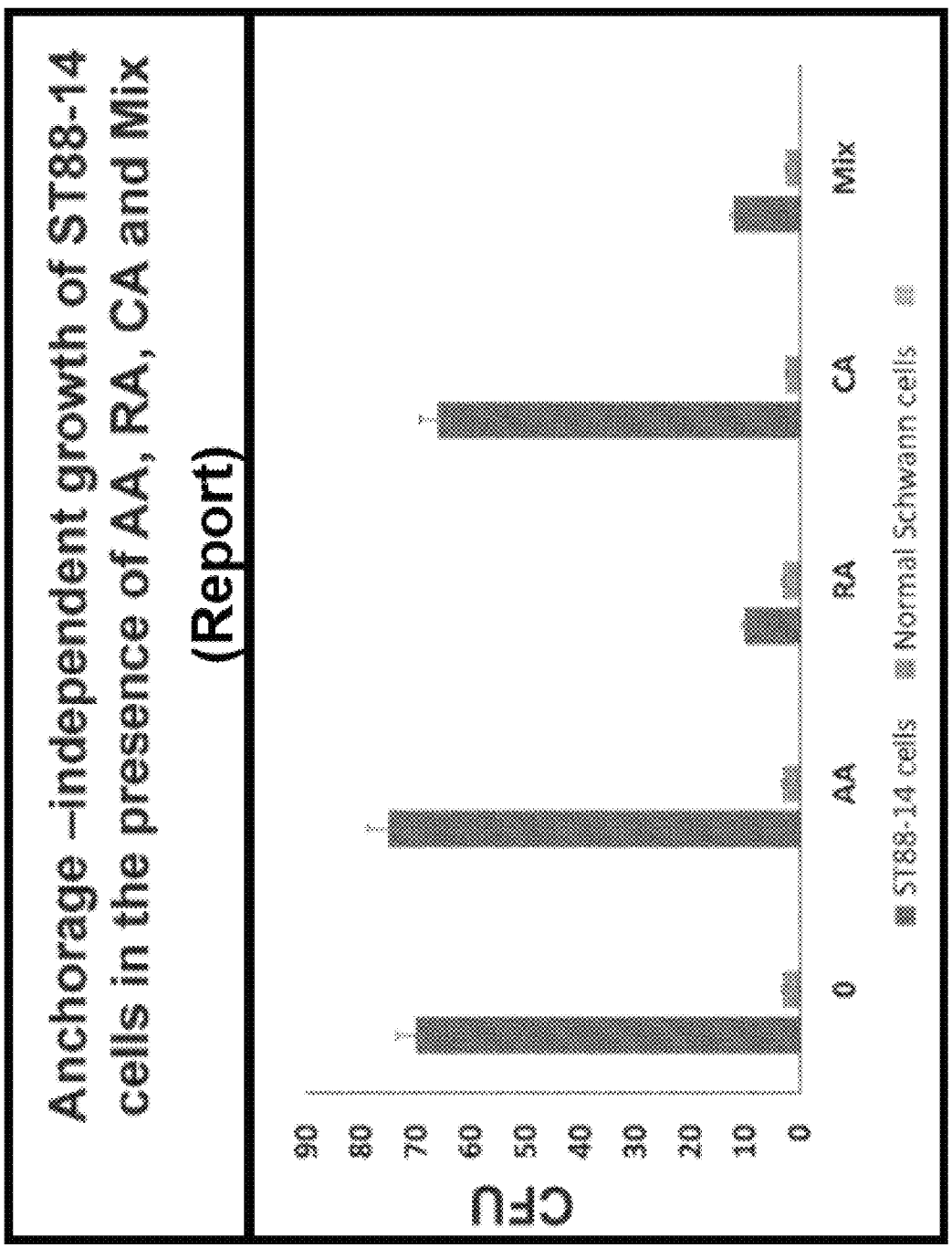
FIG. 7B illustrates a report on AA, RA, CA and mixture of three, and the colonies were counted manually, in accordance with an exemplary embodiment of the present disclosure.
Figure 7C:
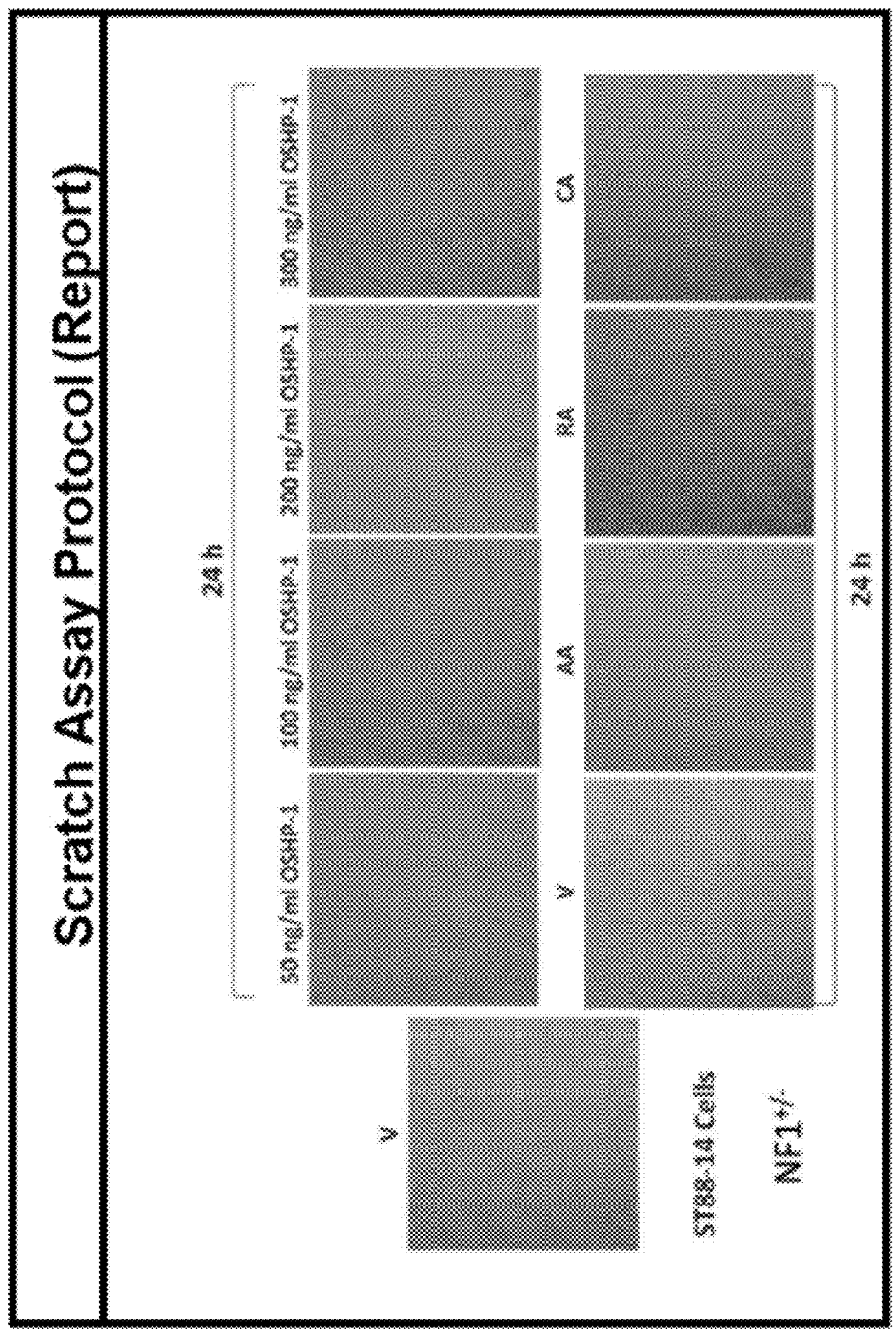
FIG. 7C illustrates a report on a scratch assay protocol performed using ST88-14 cells in the absence or presence of OSHP-1, AA, RA, CA, in accordance with an exemplary embodiment of the present disclosure. The data suggest that it is the RA component of OSHP-1 that is responsible for the blocking the anchorage independent growth, invasion and metastasis of MPNSTs, FIG. 7D illustrate a report on test whether and AA, RA, and CA affect the invasiveness of human metastatic melanoma, in accordance with an exemplary embodiment of the present disclosure. Scratch assay results show that OSHP-1 inhibits the migration of cells and RA component in OSHP-1 is the one contributing to this property.
Figure 7D:
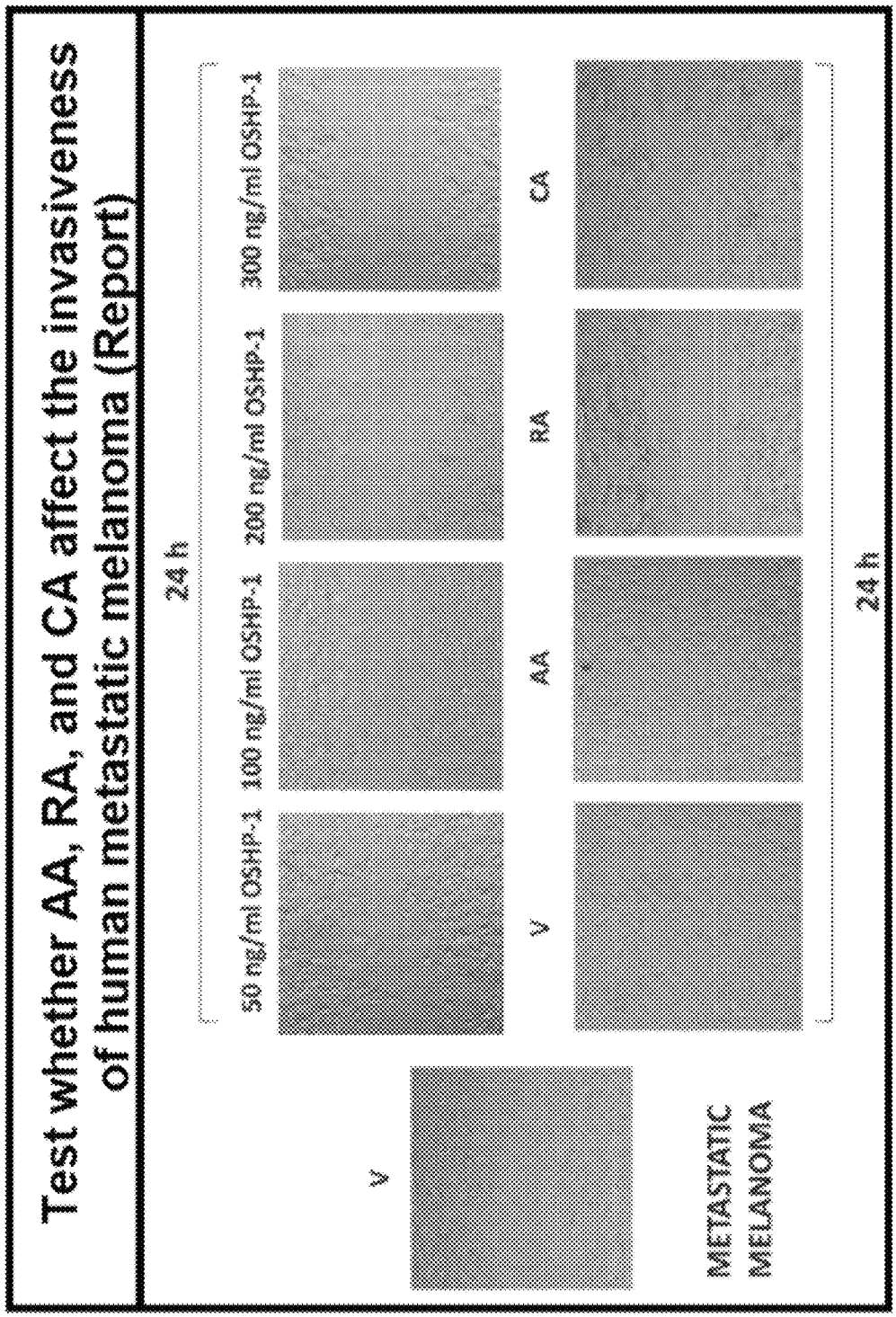
Figure 8A:
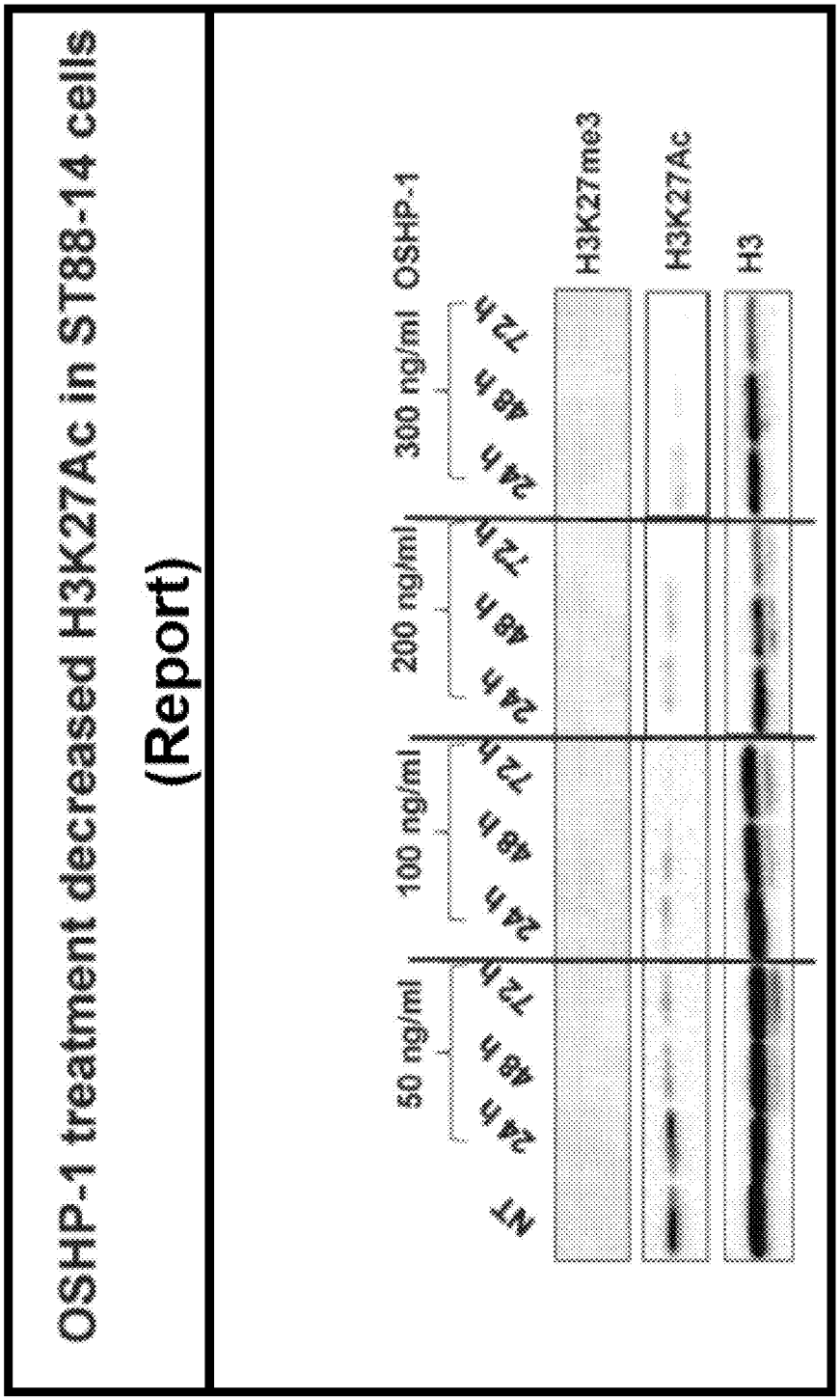
FIG. 8A illustrates a report on effect of OSHP-1 on H3K27 acetylation, where Histone proteins were extracted from ST88-14 cells after treating with the indicated amounts of OSHP-1 for 24, 48 and 72 hand immunoblotted by H3K27Ac antibody, in accordance with an exemplary embodiment of the present disclosure. The results show that OSHP-1 treated cells showed a does dependent and time dependent decrease in H3K27 acetylation.
Figure 8B:
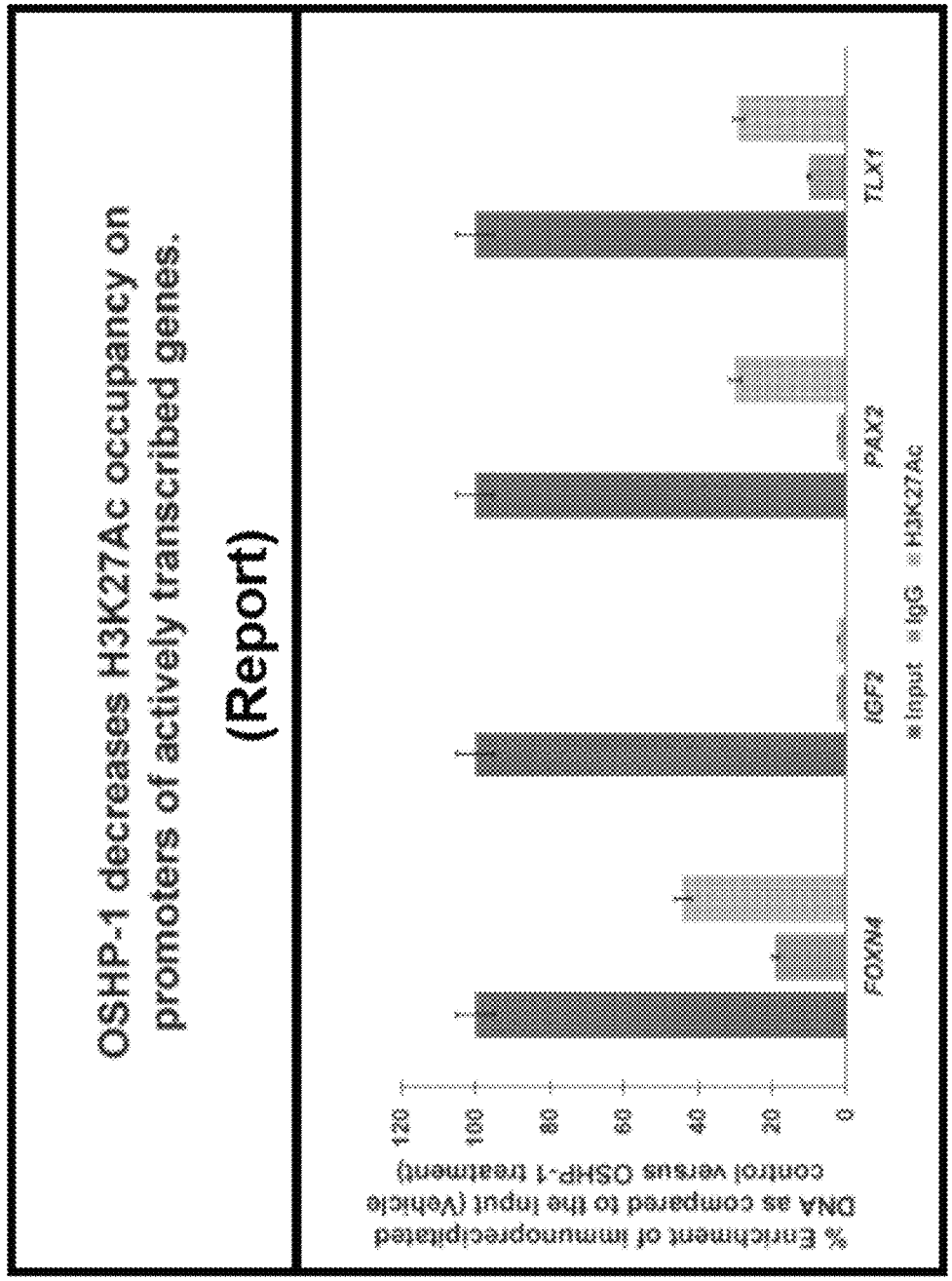
FIG. 8B illustrates a report on Chromatin immunoprecipitation of treated OSHP-1 treated (48 h) ST88-14 cells using H3K27Ac and control IgG show that there is a significant decrease in the promoter occupancy of H3K27Ac on key tumorigenic genes, in accordance with an exemplary embodiment of the present disclosure.

Effect of OSHP-1 on anchorage independent growth or metastasis. To determine whether OSHP-1 and its individual components can block the anchorage independent growth of ST-8814 cells, and Normal Human Schwann by subjecting the cells to Soft Agar colony formation assays in the absence and presence of OSHP-1, AA, RA, CA and mixture of three, and the colonies were counted manual. Additionally, a scratch assay protocol was performed using ST88-14 cells in the absence or presence of OSHP-1, AA, RA and CA The data (FIGS. 7A, 7B and 7C) suggest that is the RA component of OSHP-1 that is responsible for the blocking of anchorage independent growth, invasion and metastasis of MPNSTs. Additionally, we also tested whether OSHP-1 and AA, RA, and CA affect the invasiveness of human metastatic melanoma. Scratch assay results in FIG. 7D shows that OSHP-1 inhibits the migration of cells and RA component in OSHP-1 is the one contributing to this property.

Effect of OSHP-1 on H3K27 acetylation. Total histone isolated from OSHP-1 treated ST88-14 cells showed a does dependent and time dependent decrease in H3K27 acetylation (Fig. SA), as well as decrease in the promoter occupancy of H3K27Ac on key tumorigenic genes (Fig. SB).

Figure 9:
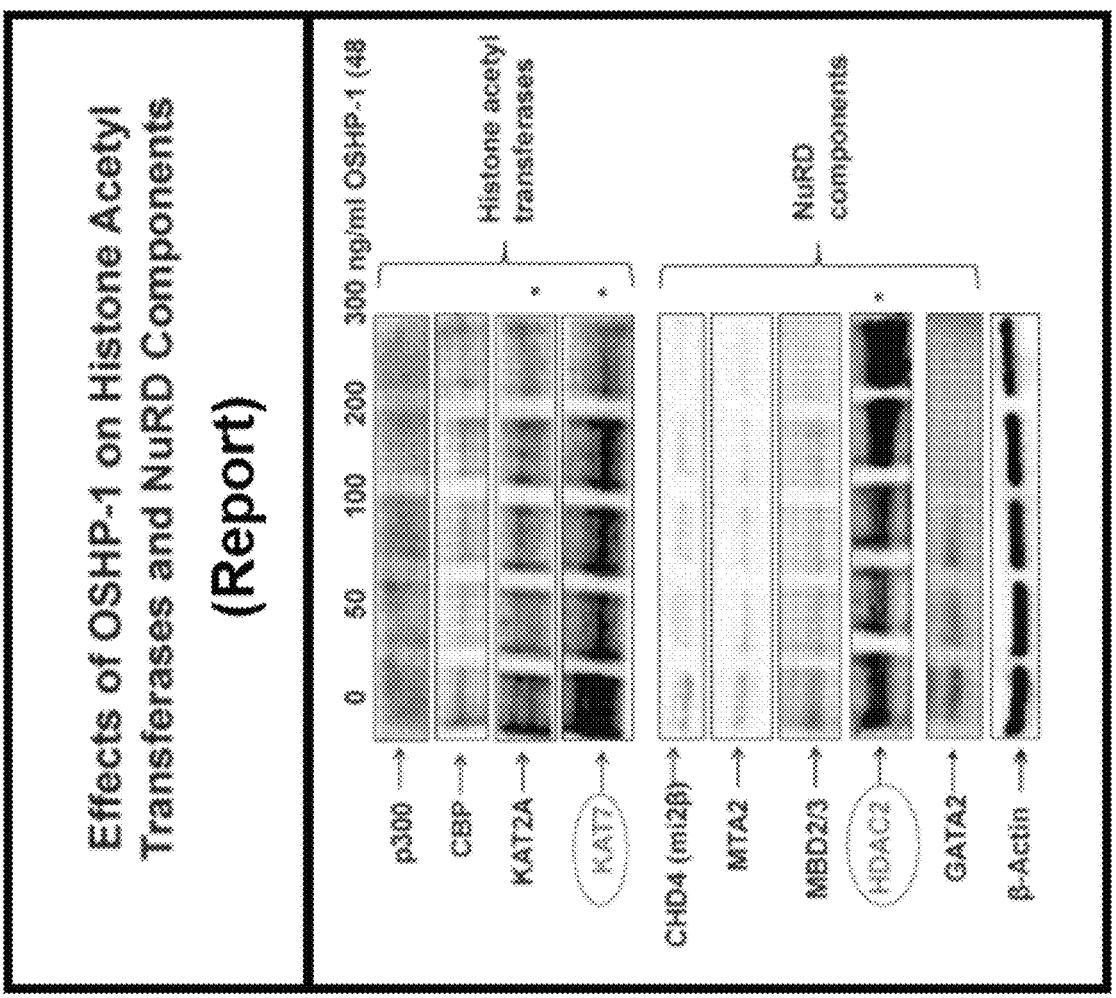
FIG. 9 illustrates a report on effect of OSHP-1 on histone acetyl transferases and Nucleosome remodeling deacetylases (NuRD): Nuclear fraction from ST88-14 cells were isolated following treatment with the indicated amounts of OSHP-1 (50-300 ng/ml) for 48 h, and immunoblotted by using p300, in accordance with an exemplary embodiment of the present disclosure. CBP, KAT2A, KAT7 acetyl transferases and CHD4, MTA2, MBD2/3, HDAC2, GATA 2 (NuRD) components and b-actin antibodies. The results indicated that OSHP-1 decreased the activity of lysine acetyltransferase 7 (KAT 7) as well as increased the activity of HDAC2 in a dose dependent manner.

Effect of OSHP-1 on histone acetyl transferases and Nucleosome remodeling deacetylases (NuRD). Immunoblots of nuclear extracts isolated from OSHP-1 (50-300 ng/ml) treated ST88-14 cells showed that lysine acetyl transferase KAT 7 activity decreased and HDAC2 activity increased in a dose dependent manner (FIG. 9).

Figure 10:
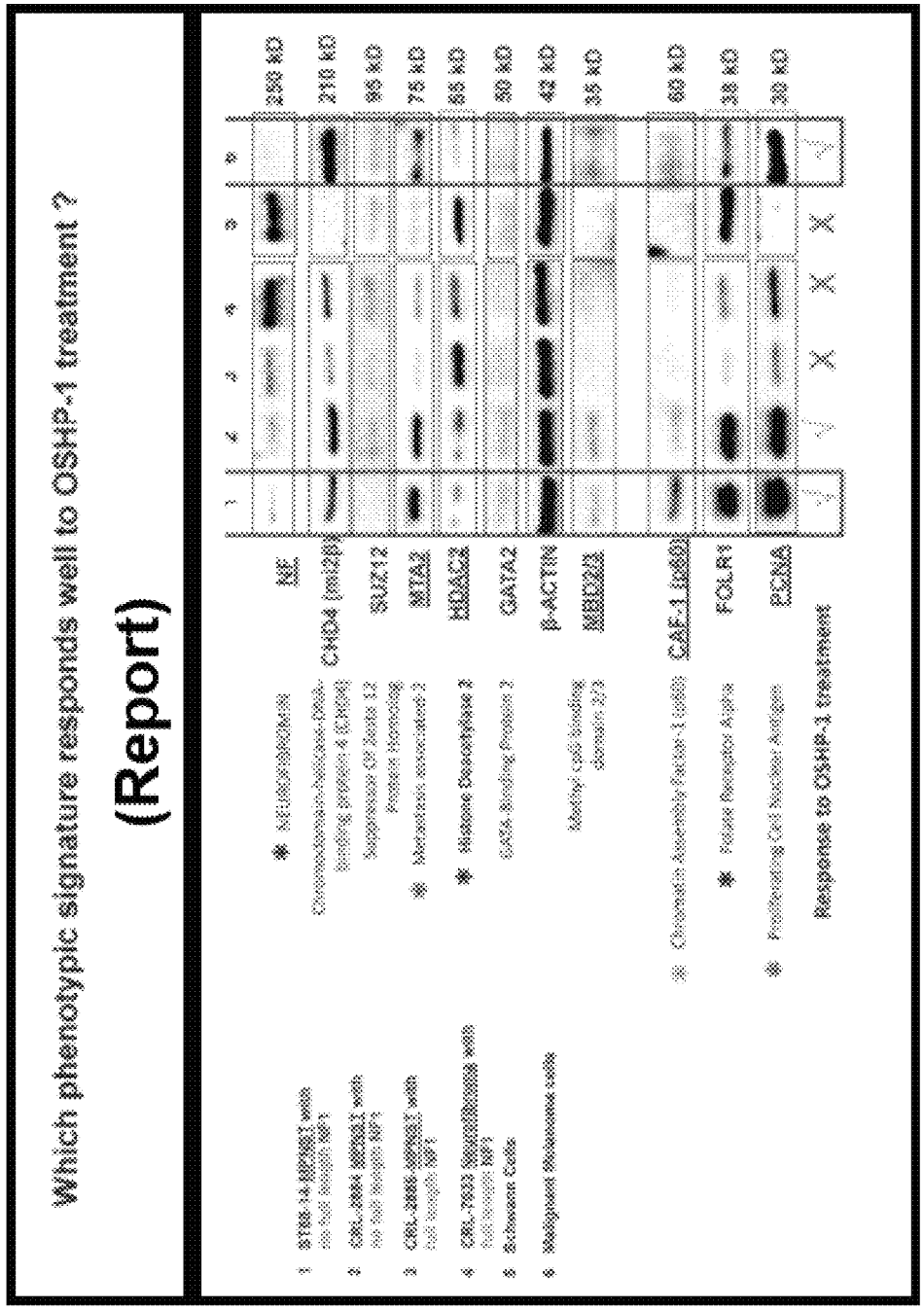
FIG. 10 illustrates a report on phenotypic signatures in cancers/tumors that responds well to OSHP-1 treatment are (a) loss of NFI, (b) increased expression of MTA2; (c) a decreased expression of HDAC2, (d) presence of methyl cpG binding domain 2/3 protein, (e) increased expression of chromatin assembly factor I (p60), (f) increased expression of FOLRI (FRa) and (g) increased expression of proliferating cell nuclear antigen (PCNA).

Which phenotypic signatures respond well to OSHP-1 treatment? In an attempt to know which kinds of cancers/tumors respond well to OSHP-1 treatment, we performed immunoblots of various phenotypic signatures and discovered which OSHP-1 is very effective as an antitumor/anticancer treatment, composition for cancers/tumors which have the phenotypic signatures as follows:
(a) loss of NF1;
(b) increased expression of MTA2:
(c) a decreased expression of HDAC2:
(d) presence of methyl cpG binding domain 2/3 protein,
(e) increased expression of chromatin assembly factor I (P60);
(f) increased expression of FOLR1 (FRa) and (g) increased expression of proliferating cell nuclear antigen (PCNA) (FIG. 10).

Neurofibromatosis type I (NF1) is common, occurring 1/3000 live births, and results in skin pigmentation and the growth of tumors along nerves in the skin brain, and other parts of the body. It arises from a mutated and nonfunctional tumor suppressor bearing its name. Tumors of the peripheral nerves, called neurofibromas, and of the main eye nerve, called optic glioma, are debilitating and deadly. Neurofibromas contain cancerous NFI-deficient Schwann cells as well as $NF1^{+/-}$ mast cells, endothelial cells and fibroblasts that contribute to neurofibroma and growth. Optic glioma is composed of NF 1-deficient neoplastic glial cell types (astrocytes, glioma stem cells) coupled with $NF1^{+/-}$ astrocytes, neurons and and microglia. Although there are several human clinical trials underway, there is no known cure or treatment of NF1-MPNST.

We discovered steps leading to the loss of a subset of cells in the nervous system called the Schwann cells that become tumors. In this invention, we are putting forth an entirely novel approach by which the growth of these Schwann that form tumors can be arrested, and the same cells can be made to function as normal Schwann cells by a novel compound called *Ocimum Sanctum* hydrophilic fraction (OSHP-1) which interferes with the proteins called histones that sit on the DNA and remodels them in a manner that stops the bad cancer genes from expressing. Obviously, before trying this new investigational drug on humans, it must be tested on the animal model of the human disease.

An anti-tumor or an anti-cancer drug or a combination of drug in combination therapy is effective only if it fulfils the following:
1) Decrease in proliferation;
2) Decrease in tumorigenic gene expression;
3) Decrease in self-renewal;
4) Decrease anchorage independent growth; or Decrease in metastatic growth potential
5) Increase differentiation or re-differentiation.

Our goal was to look for these parameters in a drug or a combination of drugs to specifically treat malignant neurofibromas of the peripheral nerve sheath. We have isolated and purified an active compound from *Ocimum Sanctum* leaves called the *Ocimum Sanctum* Hydrophilic fraction-I (OSHP-1). Mass Spec analysis of HPLC OSHP-1 fraction revealed that it consists of a mixture of ascorbic acid. rosmarinic acid, caffeoylquinic Acid and glycosyl sulfones.

Individually ascorbic acid increased the HDAC2 and decreased KAT7 levels; rosmarinic acid decreased metastasis as observed in scratch assays, and caffeoylquinic acid promoted differentiation of MPNST cells and decreased self-renewal by decreasing SOX2 expression in vitro. The combined effect was decrease in proliferation, tumorigenic gene expression, self-renewal anchorage independent growth. metastatic potential and increase in differentiation.

Dissection of the mechanism of OSHP-1 action by studying the effects of individual and combination of components of OSHP-I on MPNST ceil ST88-14.

Caffeoylquinic Acid: Caffeoylquinic Acid ingredient of OSHP-I increases NCAM and p75 and decreases Lysine acetyl transferase 7 (KAT7) in the nuclear extract. NCAM (140 KD) and p75 are the marker of differentiated Schwann Cells. SOX2 is responsible for increasing the cancer stem cell proliferation. Caffeoylquinic acid decreases SOX2 expression. Thus, the differentiation of MPNST cells that we observe with caffeoylquinic acid ingredient of OSHP-1 is by at least three mechanisms. (1) Increase NCAM and p75 levels; (2) Decrease in SOX2 expression; (3) Decrease in lysine acetyltransferase 7 (KAT7) thereby reducing the acetylation of histones H3 (H3K27Ac) and reducing gene activation.

Ascorbic Acid: Ascorbic acid is one of the ingredients of OSHP-1 which reduces the KAT-7 activity and increases HDAC2 activity thereby reducing the acetylation of H3 on K27. The result is that there is decreased H.3K27Ac occupancy on the enhancer/promoter of proliferative genes.

Rosmarinic Acid: The function of Rosmarinic acid component in OSHP-1 is to block metastasis or cell invasion.

This was tested not only in NF1$^{+/-}$ cell line ST88-14, but also in metastatic melanoma cell line. OSHP-1 is very effective as an anti-tumor/anti-cancer treatment composition for cancers/tumors which have the phenotypic signatures as follows: (a) loss of NF1; (b) increased expression of MTA2; (c) a decreased expression of HDAC2; (d) presence of methyl cpG binding domain 2/3 protein; (e) increased expression of chromatin assembly factor I (p60); (t) increased expression of FOLRI (FRa) and (g) increased expression of proliferating cell antigen (PCNA).

The advantage of presently claimed invention is a pharmaceutical composition and a bioactive hydrophobic extract from *Ocimum Sanctum* is capable of treating cancer, especially MPNST or Neurofibromas and metastatic melanoma by promoting differentiation.

What is claimed is:

1. A non-naturally occurring pharmaceutical composition comprising components with a weight ratio of,
   i. ascorbic acid in a range of about 0.8 to 1.2,
   ii. caffeoylquinic acid in a range of about 2 to 5,
   iii. rosmarinic acid in a range of about 0.6 to 1,
   iv. glycosyl sulfones in a range of about 2 to 2.6,
   v. one or more of: a pharmaceutically acceptable carrier; diluent;
   and/or additives;
   vi. wherein the ratio of the components is maintained in the pH range of about 5.5 to 8;
   prepared by
   a) preparing a mixture of *Ocimum Sanctum* in water, wherein a ratio of *Ocimum Sanctum* to water is 1:100, and wherein the *Ocimum Sanctum* is in a powder form, and boiling the mixture for a predetermined time to obtain a boiled mixture;
   b) cooling the boiled mixture to a room temperature and centrifuged at 3000×g for a predetermined time minutes to obtain a supernatant;
   c) isolating the supernatant and adjusting the pH of the supernatant in a range of 6.8 to 7.6 to obtain a solution;
   d) lyophilizing the solution of step (c) to obtain a powder;
   e) suspending the powder in 80% methanol to obtain a powder-organic solvent mixture;
   f) stirring the powder-organic solvent mixture for a predetermined duration to obtain an organic solvent mixture;
   g) centrifuging at 3000×g the powder-organic solvent mixture for a predetermined time to obtain an organic fraction; and
   h) lyophilizing the organic fraction to obtain the pharmaceutical composition.

2. The pharmaceutical composition according to claim 1, wherein the pharmaceutically acceptable carrier is selected from the group consisting of microspheres, nanotubes, nanoparticles, nanofibers, peptides any other pharmaceutically acceptable carriers for delivery and/or any combination of these delivery methods.

3. The pharmaceutical composition according to claim 1, wherein the diluent is selected from the group consisting of lactose, mannitol, sorbitol, microcrystalline cellulose, sucrose, sodium citrate, di-calcium phosphate or mixture thereof.

4. The pharmaceutical composition according to claim 1, wherein the pharmaceutical composition is in the form of a solid, and able to be made into a liquid or a lyophilized formulation.

5. The pharmaceutical composition according to claim 1, wherein the additives are selected from the group consisting of glycols, Hyaluronic acid, sodium hyaluronate, and surface-active agents.

6. A process for preparation of a bioactive fraction of *Ocimum Sanctum* hydrophilic fraction-I from plant *Ocimum Sanctum* comprising the steps of:
   a) preparing mixture of *Ocimum Sanctum* in water, wherein a ratio of *Ocimum Sanctum* to water is 1:100, and wherein the *Ocimum Sanctum* is in a powder form, and boiling the mixture for a predetermined time to obtain a boiled mixture;
   b) cooling the boiled mixture to a room temperature and centrifuged at 3000×g for a predetermined time minutes to obtain a supernatant;
   c) isolating the supernatant and adjusting the pH of the supernatant in a range of 6.8 to 7.6 to obtain a solution;
   d) lyophilizing the solution of step (c) to obtain a powder;
   e) suspending the powder in 80% methanol to obtain a powder-organic solvent mixture;
   f) stirring the powder-organic solvent mixture for a predetermined duration to obtain an organic solvent mixture;
   g) centrifuging at 3000×g the powder-organic solvent mixture for a predetermined time to obtain an organic fraction; and
   h) lyophilizing the organic fraction to obtain the bioactive fraction in a pharmaceutical composition in a powder form comprising in the weight ratio:
      i. ascorbic acid is in a range of about 0.8 to 1.2,
      ii. caffeoylquinic acid is in a range of about 2 to 5,
      iii. rosmarinic acid is in a range of about 0.6 to 1, and
      iv. glycosyl sulfones is in a range of about 2 to 2.6.

7. The process according to claim 6, wherein the *Ocimum Sanctum* leaf powder is dried leafpowder.

8. The process according to claim 6, wherein the pH of the solution in step c) is adjusted to 7.2.

9. The process according to claim 6, wherein the organic solvent is selected from the group consisting of alcoholic solvents comprising methanol, ethanol, 1-propanol, 2-propanol, cyclohexanol, methyl cyclohexanol, and ether solvent comprising dimethyl ether, diethyl ether, ethyl methyl ether, t-butyl ether, and tetrahydrofuran.

10. The process according to claim 6, wherein the powder obtained is further dissolved in an alcoholic solvent, wherein the alcoholic solvent is selected from the group consisting of methanol, ethanol, 1-propanol, 2-propanol, cyclohexanol, methyl cyclohexanol.

11. A method for the treatment of malignant neurofibroma by administrating suitable amount of a pharmaceutical composition having, in weight ratio, of:
   i. ascorbic acid is in a range of about 0.8 to 1.2,
   ii. caffeoylquinic acid is in a range of about 2 to 5,
   iii. rosmarinic acid is in a range of about 0.6 to 1, and
   iv. glycosyl sulfones is in a range of about 2 to 2.6;
   or a bioactive fraction prepared by
   a) preparing mixture of *Ocimum Sanctum* in water, wherein a ratio of *Ocimum Sanctum* to water is 1:100, and wherein the *Ocimum Sanctum* is in a powder form, and boiling the mixture for a predetermined time to obtain a boiled mixture;
   b) cooling the boiled mixture to a room temperature and centrifuged at 3000×g for a predetermined time minutes to obtain a supernatant;
   c) isolating the supernatant and adjusting the pH of the supernatant in a range of 6.8 to 7.6 to obtain a solution;
   d) lyophilizing the solution of step (c) to obtain a powder;

e) suspending the powder in 80% methanol to obtain a powder-organic solvent mixture;

stirring the powder-organic solvent mixture for a predetermined duration to obtain an organic solvent mixture;

g) centrifuging at 3000×g the powder-organic solvent mixture for a predetermined time to obtain an organic fraction; and h) lyophilizing the organic fraction to obtain the bioactive fraction in powder form comprising in the weight ratio:
　i. ascorbic acid is in a range of about 0.8 to 1.2,
　ii. caffeoylquinic acid is in a range of about 2 to 5,
　iii. rosmarinic acid is in a range of about 0.6 to 1, and
　iv. glycosyl sulfones is in a range of about 2 to 2.6;
or any combination thereof.

12. The method according to claim 11, wherein the malignant neurofibroma is peripheral nerve sheath and other neural crest cell-derived tumors having a lineage from neural crest, melanocytic tumors, peripheral neuroblastic, embryonal tumors of the CNS including medulloblastoma, atypical teratoid/rhabdoid tumor and CNS/supratentorial primitive neuroectodermal paraganglioma, and other tumors of neural crest origin comprising medullary thyroid carcinoma.

13. The method according to claim 11, wherein the carcinoma cells may be from cells and tissues derived from neural crest during the development process, including but not limited to various cranial and craniofacial cartilages and melanocytes, adrenal medulla, arteries, etc.

14. The method according to claim 11, wherein method of administration is oral route, sublingual and buccal routes, rectal route, vaginal route, ocular optic route or nasal route, and topical route.

15. A non-naturally occurring pharmaceutical composition consisting of components with a weight ratio of,
　i. ascorbic acid in a range of about 0.8 to 1.2,
　ii. caffeoylquinic acid in a range of about 2 to 5,
　iii. rosmarinic acid in a range of about 0.6 to 1,
　iv. glycosyl sulfones in a range of about 2 to 2.6,
　v. one or more of: a pharmaceutically acceptable carrier; diluent; and/or additives; and
　vi. wherein the ratio of the components is maintained in the pH range of about 5.5 to 8.

* * * * *